(12) United States Patent
Lee et al.

(10) Patent No.: US 12,290,585 B2
(45) Date of Patent: May 6, 2025

(54) POROUS COMPOSITE POWDER FOR ADSORPTION OF FINE DUST AND METHOD FOR MANUFACTURING THE SAME

(71) Applicant: AMOREPACIFIC CORPORATION, Seoul (KR)

(72) Inventors: Hyunsuk Lee, Yongin-si (KR); Jaewon You, Yongin-si (KR); Hye Won Na, Yongin-si (KR); Bokyung Jung, Yongin-si (KR); Chang Jo Jung, Yongin-si (KR); Nari Cha, Yongin-si (KR); Sangkyun Chae, Yongin-si (KR); Sohyun Hong, Yongin-si (KR)

(73) Assignee: AMOREPACIFIC CORPORATION, Seoul (KR)

(*) Notice: Subject to any disclaimer, the term of this patent is extended or adjusted under 35 U.S.C. 154(b) by 191 days.

(21) Appl. No.: 17/342,278

(22) Filed: Jun. 8, 2021

(65) Prior Publication Data
US 2021/0386634 A1 Dec. 16, 2021

(30) Foreign Application Priority Data

Jun. 10, 2020 (KR) ........................ 10-2020-0070512
May 26, 2021 (KR) ........................ 10-2021-0067802

(51) Int. Cl.

| | |
|---|---|
| *A61K 8/29* | (2006.01) |
| *A61K 8/02* | (2006.01) |
| *A61K 8/04* | (2006.01) |
| *A61K 8/19* | (2006.01) |
| *A61K 8/20* | (2006.01) |
| *A61K 8/25* | (2006.01) |
| *A61K 8/26* | (2006.01) |
| *A61K 8/27* | (2006.01) |
| *A61K 8/49* | (2006.01) |
| *A61K 8/73* | (2006.01) |
| *A61K 8/85* | (2006.01) |
| *A61K 8/88* | (2006.01) |
| *A61Q 19/00* | (2006.01) |
| *A61Q 19/10* | (2006.01) |

(52) U.S. Cl.
CPC ................ *A61K 8/29* (2013.01); *A61K 8/025* (2013.01); *A61K 8/0279* (2013.01); *A61K 8/046* (2013.01); *A61K 8/19* (2013.01); *A61K 8/20* (2013.01); *A61K 8/25* (2013.01); *A61K 8/26* (2013.01); *A61K 8/27* (2013.01); *A61K 8/498* (2013.01); *A61K 8/731* (2013.01); *A61K 8/736* (2013.01); *A61K 8/737* (2013.01); *A61K 8/85* (2013.01); *A61K 8/88* (2013.01); *A61Q 19/008* (2013.01); *A61Q 19/10* (2013.01); *A61K 2800/412* (2013.01); *A61K 2800/80* (2013.01); *A61K 2800/805* (2013.01)

(58) Field of Classification Search
None
See application file for complete search history.

(56) References Cited

U.S. PATENT DOCUMENTS

| | | | |
|---|---|---|---|
| 9,017,812 | B2 | 4/2015 | Takezaki et al. |
| 9,616,002 | B2 | 4/2017 | Gonzales et al. |
| 2016/0067152 | A1 | 3/2016 | Franklin et al. |
| 2016/0194209 | A1 | 7/2016 | Yuan et al. |
| 2018/0042823 | A1 | 2/2018 | Lee et al. |
| 2018/0133115 | A1 | 5/2018 | Lee et al. |
| 2018/0215892 | A1 | 8/2018 | Girod Fullana et al. |
| 2019/0040224 | A1 | 2/2019 | Lee et al. |
| 2021/0128428 | A1* | 5/2021 | Pagis ..................... A61K 8/99 |

FOREIGN PATENT DOCUMENTS

| | | |
|---|---|---|
| CN | 103849003 A | 6/2014 |
| CN | 107427444 A | 12/2017 |
| CN | 108040466 A | 5/2018 |
| CN | 108366918 A | 8/2018 |
| CN | 110812276 A | 2/2020 |
| JP | 2019099947 A * | 6/2019 |
| JP | 2020-26429 * | 2/2020 |
| KR | 10-0431244 B1 | 5/2004 |
| KR | 10-1382732 B1 | 4/2014 |
| KR | 10-1649798 B1 | 8/2016 |
| KR | 10-1818935 B1 | 1/2018 |
| KR | 10-2019-0057711 A | 5/2019 |
| KR | 2019-0139566 * | 12/2019 |
| KR | 10-2020-0017820 A | 2/2020 |

OTHER PUBLICATIONS

English translation for JP2020-26429 (2020).*
English translation for JP2020-26429 claims (2020).*
English translation for KR2019-0139566 (2019).*
English translation for JP 2019-99947. (Year: 2019).*
Naji et al ("Performance Evaluation of Asphalt Concrete Mixes Containing Granular Volcanic Ash", Journal of Materials in Civil Engineering, vol. 20 (12) (Dec. 2008), p. 1-28, obtained at the website: 35-VolcanicAsh.pdf) (Year: 2008).*
Yin Yuan et al., "Modification of porous PLGA microspheres by poly-l-lysine for use as tissue engineering scaffolds", Colloids and Surfaces B: Biointerfaces, vol. 161: 162-168 (2018).
Farah Hanani Zulkifli et al., "Highly porous of hydroxyethyl cellulose biocomposite scaffolds for tissue engineering", International Journal of Biological Macromolecules, vol. 122: 562-571 (2019).
Office Action for Chinese Patent Application No. 2021106496744 (Sep. 5, 2023).

* cited by examiner

*Primary Examiner* — Sin J Lee
(74) *Attorney, Agent, or Firm* — Merchant & Gould P.C.

(57) ABSTRACT

The present disclosure provides porous composite powder which includes biodegradable polymer particles with a porous structure having positive charges dispersed uniformly thereon and further includes inorganic particles. The porous composite powder adsorbs and removes fine particulate matter remaining in the skin and skin pores effectively through ionic bonding, while maintaining a spherical shape. The present disclosure also provides a method for preparing porous composite powder for adsorption of fine dust including particles forming a composite homogeneously, while maintaining a spherical shape, through a single process.

7 Claims, 30 Drawing Sheets

Mag = 1.50 K X
Aperture size = 30.00 µm
GeminiSEM 300-70-24

WD = 9.4 mm
Scan Speed = 5
Noise Reduction-Line Int. Busy N=35
EHT = 1.50 kV

Signal A = SE2
ESB grid is = 300V

Date: 10 Oct 2019 Time: 14:32:13
System Vacuum = 3.44e-006 mbar

Mag = 10.00 K X
Aperture size = 10.00 μm
GeminiSEM 300-70-24

WD = 9.4 mm
Scan Speed = 5
Noise Reduction-Line Int. Busy N=35
EHT = 1.50 kV

Signal A = SE2
ESB grid is = 300V

Date: 10 Oct 2019 Time: 14:35:02
System Vacuum = 3.27e-006 mbar

Mag = 2.00 K X
Aperture size = 30.00 µm
GeminiSEM 300-70-24

WD = 10.4 mm
Scan Speed = 3
Noise Reduction=Line Int. Busy N=23
EHT = 2.00 kV

Signal A = SE2
ESB grid is = 300V

Date: 15 May 2020 Time: 10:17:06
System Vacuum = 4.34e-006 mbar

Mag = 10.00 K X
Aperture size = 30.00 µm
GeminiSEM 300-70-24

Signal A = SE2
ESB grid is = 300V

WD = 10.3 mm
Scan Speed = 4
Noise Reduction=Line Int. Busy N=23
EHT = 2.00 kV

Date: 15 May 2020 Time: 10:22:38
System Vacuum = 3.58e-006 mbar

Mag = 10.00 K X
Aperture size = 30.00 µm
GeminiSEM 300-70-24

WD = 9.4 mm
Scan Speed = 5
Noise Reduction-Line Int. Busy N=35
EHT = 1.50 kV

Signal A = SE2
ESB grid is = 300V

Date: 10 Oct 2019 Time: 14:35:02
System Vacuum = 3.27e-006 mbar

HI 98703

(a)  (b)  (c)  (d)

Mag = 5.00 K X
Aperture size = 30.00 μm
GeminiSEM 300-70-24

WD = 9.4 mm
Scan Speed = 5
Noise Reduction-Line Int. Busy N=35
EHT = 2.00 kV

Signal A = SE2
ESB grid is = 300V

Date: 13 Apr 2020 Time: 8:59:25
System Vacuum = 2.45e-006 mbar (a)          (b)          (c)

Mag = 7.48 K X
Aperture size = 30.00 μm
GeminiSEM 300-70-24

Signal A = SE2
ESB grid is = 300V

WD = 7.6 mm
Scan Speed = 4
Noise Reduction=Line Int. Busy N=45
EHT = 1.30 kV

Date: 22 May 2020 Time: 11:23:29
System Vacuum = 3.98e-006 mbar (a)      (b)      (c)

(a)      (b)      (c)

POROUS COMPOSITE POWDER FOR ADSORPTION OF FINE DUST AND METHOD FOR MANUFACTURING THE SAME

CROSS-REFERENCE TO RELATED APPLICATION

The present application claims priority to Korean Patent Application No. 10-2020-0070512 filed on Jun. 10, 2020 and Korean Patent Application No. 10-2021-0067802 filed on May 26, 2021 in the Republic of Korea, the disclosures of which are incorporated herein by reference.

TECHNICAL FIELD

The present disclosure relates to porous composite powder having an excellent effect of adsorbing fine dust and a method for manufacturing the same.

BACKGROUND ART

When dust builds up in the human body, the level of immunity is decreased, and various diseases, such as heart diseases or respiratory diseases, may occur. Dust build-up causes even bronchial stenosis, and long-term inhalation of dust increases prevalence of asthma or lung diseases and early mortality.

Particularly, the skin is the outermost part of the body that is in direct contact with dust and functions as a barrier between an organism and environment. When the skin is frequently exposed to pollutants, the barrier function is degraded. Particularly, since fine dust is 20 times smaller than the skin pores, it can easily infiltrate into the skin. In fact, it is known that air pollutants, such as fine dust, severely affects the skin health.

Dust piled up on the skin can be removed mostly by using various commercially available cleanser products. However, fine dust infiltrated into the skin pores cannot be removed with ease. Therefore, there is a need for studies about a functional composite powder structure capable of effectively removing fine dust, which is a hazardous substance harmful to the skin and causes a fatal disorder in the human body. In addition, since such a functional composite powder structure is a material functioning in the skin pores, it is important to select a safe biocompatible material causing no particular irritation.

DISCLOSURE

Technical Problem

A technical problem to be solved by the present disclosure is to adsorb and remove fine dust adhered to the skin or skin pores, or fine dust-containing sebum effectively by using porous composite powder.

Another technical problem to be solved by the present disclosure is to provide porous composite powder for adsorption of fine dust, which includes particles forming a composite homogeneously, while maintaining a spherical shape, through a single process.

Technical Solution

In one general aspect, there is provided porous composite powder for adsorption of fine dust, including: a biodegradable polymer; a cationic polymer; and inorganic particles.

In another general aspect, there is provided a composition for adsorption of fine dust, including the porous composite powder.

In still another general aspect, there is provided a method for preparing the porous composite powder for adsorption of fine dust, including the steps of: to preparing a solution including a biodegradable polymer and a cationic polymer; dispersing inorganic particles into the solution including a biodegradable polymer and a cationic polymer; and spray drying the solution including the inorganic particles dispersed therein.

Advantageous Effects

According to an embodiment of the present disclosure, the porous composite powder for adsorption of fine dust includes a cationic polymer, and thus can effectively remove negatively charged fine dust, particularly fine dust having a particle diameter of 2.5 μm or less, through ionic bonding.

According to another embodiment of the present disclosure, the porous composite powder for adsorption of fine dust uses inorganic particles as supports to maintain a spherical shape of the porous composite powder, and thus can be applied to the skin with no feeling of irritation, when the composition including the porous composite powder is applied onto the skin.

According to still another embodiment of the present disclosure, fine particulate matter contained in moisture or sebum on the skin can be absorbed into the pores of the porous composite powder for adsorption of fine dust, adsorbed strongly thereto through ionic bonding, and then settled therein to be removed.

According to yet another embodiment of the present disclosure, the method for manufacturing porous composite powder for adsorption of fine dust uses a single process of spray drying to provide porous composite powder which includes a cationic polymer forming a composite homogeneously on the surface of and/or inside of a porous polymer, and inorganic particles homogeneously dispersed on the surface of and/or inside of the porous composite powder.

BEST MODE

Figure 1:
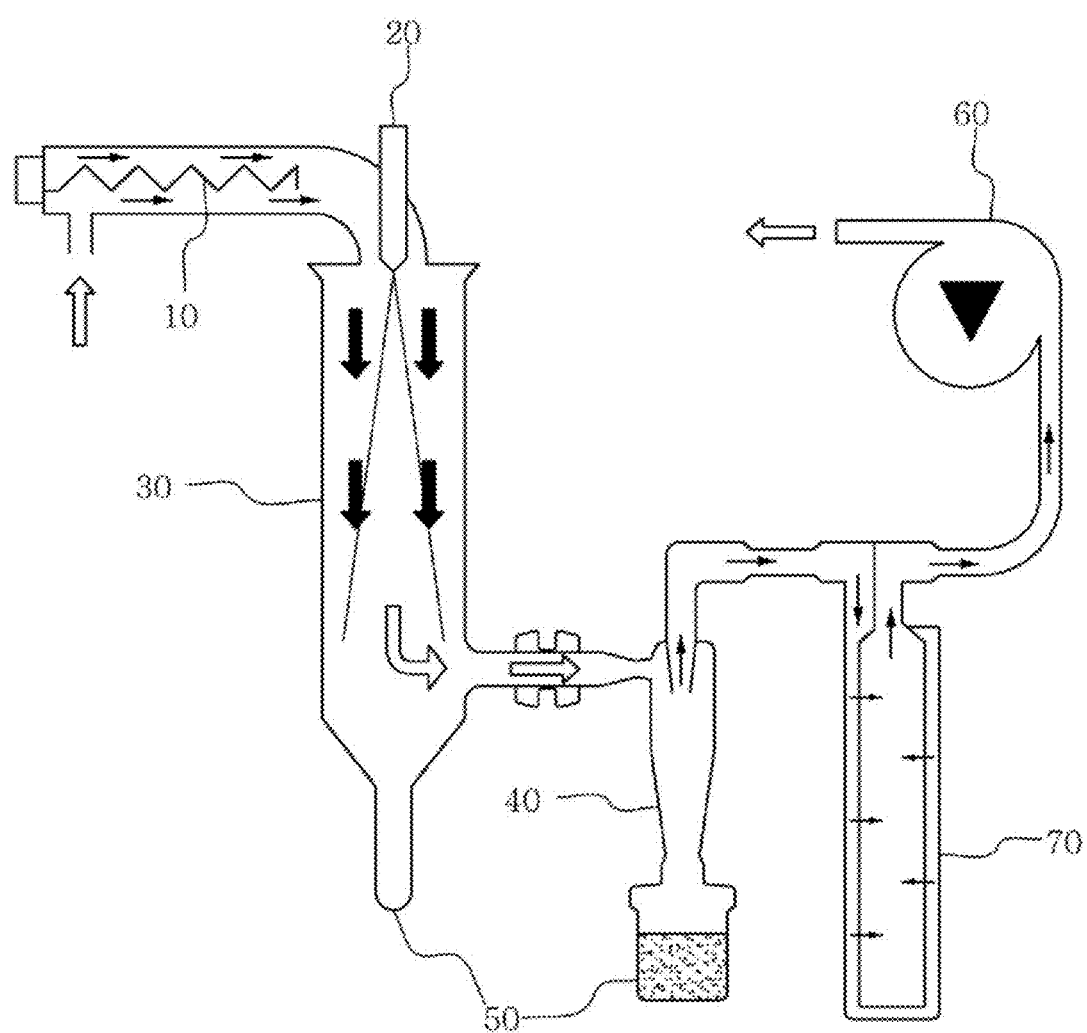
FIG. 1 is a schematic view illustrating the spray drying process according to an embodiment of the present disclosure.

Exemplary embodiments now will be described more fully hereinafter. However, the following exemplary embodiments are provided for illustrative purposes only so that the present disclosure may be understood with ease, and the scope of the present disclosure is not limited thereto.

Definition of Terms

As used herein, 'dust' collectively refers to microparticles in the atmosphere, and generally means a floating matter having a particle diameter of 10 mm or less. Particularly, dust having a particle diameter of 10 μm or less is also called 'fine dust (or particulate matter)', fine dust having a particle diameter of 2.5 μm or less, or 1 μm or less is also called 'fine particulate matter', and dust having a particle diameter of 0.1 μm or less is also called 'ultrafine particle'. Herein, 'particle diameter' may refer to the average value of diameters of individual particles. Dust is a matter including naturally occurring substances, such as sand, soil and pollen, or industrial process-derived substances, such as carbon, combusted product of carbon, metal salts and heavy metals. Dust may be present in the form of fume, mist, smoke, steam or smog. In general, dust, particularly fine dust, has a negative zeta potential value.

As used herein, 'particle diameter' means a diameter of particles, and a range of particle diameter defined herein means a range of diameter of individual single particles.

Throughout the specification, the expression 'a part includes or comprises an element' does not preclude the presence of any additional elements but means that the part may further include the other elements, unless otherwise stated.

Description of Exemplary Embodiments

Hereinafter, the present disclosure will be described in more detail.

Porous Composite Powder for Adsorption of Fine Dust

In one aspect of the present disclosure, there is provided porous composite powder for adsorption of fine dust, including: a biodegradable polymer; a cationic polymer; and inorganic particles.

The porous composite powder according to an embodiment of the present disclosure includes a cationic polymer in order to remove negatively charged fine dust effectively through ionic bonding, uses a skin- and eco-friendly biodegradable polymer, and further includes inorganic particles so that the porous composite powder may not be deformed but may retain a spherical shape.

Therefore, fine dust, particularly fine particulate matter, contained in moisture or sebum on the skin may be absorbed into the pores of the porous composite powder, adsorbed strongly thereto through ionic bonding, and then removed. In addition, the porous composite powder shows excellent settling property, and may be used advantageously as compared to the control in terms of adsorption performance.

In general, polyquaternium-based cationic polymers cause severe skin irritation and bad odor, and thus cannot be used in a large amount. Therefore, powder including a cationic polymer alone cannot be used as a cosmetic material. According to an embodiment of the present disclosure, the porous structure includes a biodegradable polymer causing no skin irritation and unpleasant odor as a basic frame thereof, and a small amount of cationic polymer is added thereto so that the porous structure may be provided with cationic property.

According to an embodiment, the biodegradable polymer and the cationic polymer may form a composite with each other. In addition, the inorganic particles may be dispersed homogeneously on the surface of the porous composite powder, inside of the porous composite powder, or both.

The porous composite powder according to an embodiment of the present disclosure is obtained through a single process using spray drying. Therefore, the biodegradable polymer and the cationic polymer form a composite with each other on the surface of the porous composite powder and/or inside thereof, and the inorganic particles are dispersed homogeneously on the surface of the porous composite powder and/or inside thereof to form a composite. In this manner, an effect of adsorbing fine dust may be realized uniformly throughout the porous composite powder, while maintaining pores having a size of several hundreds of nanometers. In addition, the porous composite powder can retain a spherical shape to provide excellent spreadability upon the application onto the skin.

Particularly, when the inorganic particles are not dispersed homogeneously on the surface of the porous composite powder and/or inside thereof, but are coated merely on the surface, the inorganic particles cannot function as supports to cause shrinking in the polymer structure, resulting in deformation of the particles. When the cationic polymer is coated and present merely on the surface, while not forming a composite, fine particulate matter with a size of less than 1 μm (micrometer) introduced into the pores cannot be adsorbed strongly thereto, but may be separated out from the pores.

According to an embodiment, the porous composite powder may be positively charged. As used herein, 'positively charged material' may refer to a material having a positive zeta potential value. The zeta potential value may be measured by the methods generally known to those skilled in the art. For example, an aqueous solution containing 0.01 wt % of a sample is prepared, 100 μL of the aqueous solution is loaded in a quartz cuvette, and then the zeta potential may be measured by using Zetasizer Nano ZS (Malvern Company).

According to an embodiment, the porous composite powder may have a zeta potential value of 1 mV or more. For example, the porous composite powder may have a zeta potential value of 1.0 mV or more, 3 mV or more, 5 mV or more, 7 mV or more, 9 mV or more, 11 mV or more, 13 mV or more, 15 mV or more, 16 mV or more, 17 mV or more, or 18 mV or more, and 100 mV or less, 90 mV or less, 80 mV or less, 70 mV or less, 60 mV or less, 50 mV or less, 40 mV or less, 30 mV or less, 25 mV or less, 23 mV or less, 20 mV or less, 19 mV or less, 18 mV or less, 17 mV or less, 16 mV or less, 15 mV or less, 14 mV or less, or 13 mV or less.

When the zeta potential value is less than 1 mV, the effect of adsorbing fine dust through ionic bonding may be degraded. When the zeta potential value is higher than 100 mV, skin irritation may occur, a bad smell may be given off, and the formulation stability may be affected adversely.

According to an embodiment, the porous composite powder may have a size of 50 μm or less. The size of the porous composite powder is determined as the maximum length thereof.

For example, the porous composite powder may have a size of 50 μm or less, 45 μm or less, 40 μm or less, 35 μm or less, 30 μm or less, 25 μm or less, 20 μm or less, 19 μm or less, 18 μm or less, 17 μm or less, 16 μm or less, 15 μm or less, 14 μm or less, 13 μm or less, 12 μm or less, 11 μm or less, 10 μm or less, 9 μm or less, 8 μm or less, 7 μm or less, 6 μm or less, 5 μm or less, 4 μm or less, 3 μm or less, 2 μm or less, or 1 μm or less, and 1 μm or more, 2 μm or more, 3 μm or more, 4 μm or more, 5 μm or more, 6 μm or more, 7 μm or more, 8 μm or more, 9 μm or more, 10 μm or more, 11 μm or more, 12 μm or more, 13 μm or more, 14 μm or more, 15 μm or more, or 20 μm or more.

When the porous composite powder has a size of larger than 50 μm, a feeling of irritation may be generated upon the application onto the skin. When the porous composite powder has a size of less than 1 μm, it is difficult to absorb sebum containing fine dust on the skin sufficiently.

As used herein, the range of size of the porous composite powder refers to a range within which 90% or more, 95% or more, or 99% or more of the porous composite powder particles fall. For example, the porous composite powder having a size that falls within a range of 50 μm or less may be 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, or 99.9% or more, based on the total number of composite powder, but is not limited thereto.

It is difficult to obtain a uniform particle size due to the characteristics of a spray drying process. Distribution of different particles sizes is more favorable to adsorption of particles. For example, this is based on the same principle as an increase in packing efficiency occurring when rice is disposed in the gaps among the beans upon the mixing of rice with beans. If the porous composite powder has a uniform particle size, contactability with the fine particulate matter present in the voids among the particles is reduced, resulting in a significant decrease in adsorption efficiency. Therefore, according to an embodiment of the present disclosure, the porous composite powder has distribution of different particles sizes within the above-defined range (50 μm or less) capable of sufficient adsorption of fine dust, while not causing a feeling of irritation. This is more favorable to complete adsorption of fine particulate matter.

The porous composite powder may have a pore size of 10 nm to 1 μm. For example, the pore size may be 10 nm or more, 30 nm or more, 50 nm or more, 70 nm or more, 100 nm or more, 150 nm or more, 200 nm or more, 350 nm or more, 400 nm or more, 450 nm or more, 500 nm or more, 550 nm or more, 600 nm or more, 650 nm or more, 700 nm or more, 750 nm or more, 800 nm or more, 850 nm or more, 900 nm or more, or 950 nm or more, and 1 μm or less, 950 nm or less, 900 nm or less, 850 nm or less, 800 nm or less, 750 nm or less, 700 nm or less, 650 nm or less, 600 nm or less, 550 nm or less, 500 nm or less, 450 nm or less, 400 nm or less, 350 nm or less, 300 nm or less, 250 nm or less, 200 nm or less, 150 nm or less, 100 nm or less, 70 nm or less, 40 nm or less, or 20 nm or less.

When the pore size is less than 10 nm, it is difficult to absorb fine dust-containing sebum. When the pore size is larger than 1 μm, the porous composite powder particles may be broken with ease due to the degradation of mechanical strength.

The porous composite powder according to an embodiment of the present disclosure has pores having a size of several nm (nanometer) to 1 μm (micrometer), can adsorb not only fine particulate matter (PM2.5) with a size of 2.5 μm or less but also fine particulate matter (PM1.0) with a size of 1 μm or less into the pores thereof, and can adsorb fine particulate matter or fine dust with a size not adsorbed in the pores on the surface thereof. In this manner, the porous composite powder can remove fine particulate matter or fine dust from the skin.

In the case of fine particulate matter, it has a distribution of different particle diameters and includes a significant amount of particles with a size of 1 μm or less. Such particles with a size of 1 μm or less are more harmful, since fine particulate matter has a higher possibility of skin permeation, and thus a means for removing such particles is essentially required. However, such particles cannot be removed with ease by the conventional materials and formulation technologies. On the contrary, the porous composite powder according to an embodiment of the present disclosure is more favorable to adsorption of particles with a size of 1 μm or less through the principles, such as osmosis, as compared to the conventional particles having pores with a large size.

According to an embodiment, the porous composite powder may have a porosity of 30-80%. For example, the porous composite powder may have a porosity of 30% or more, 35% or more, 40% or more, 45% or more, 50% or more, 55% or more, or 60% or more, and 80% or less, 75% or less, 70% or less, or 65% or less. The porosity means a ratio of pores which can actually absorb sebum containing fine dust based on the total volume. When the porosity is less than 30%, it is not possible to obtain a sufficient effect of adsorbing fine dust. When the porosity is larger than 80%, the porous composite powder has poor mechanical strength, and thus may be deformed or broken with ease.

According to an embodiment, the biodegradable polymer may be at least one selected from the group consisting of polylactic acid (PLA), polyglycolic acid (PGA), polylactic-co-glycolic acid (PLGA), polycaprolactone (PCL), cellulose and derivatives thereof. According to the present disclosure, such a biodegradable polymer is used to avoid an issue related with plastic microbeads and to improve the bio-affinity to the skin, even though the porous composite powder functions inside of the skin pores.

According to an embodiment, the cationic polymer may be at least one selected from the group consisting of polyquaternium-based compounds, cationic guar gum derivatives, chitosan and polylysine.

According to an embodiment, the cationic polymer may be at least one selected from the group consisting of Polyquaternium-4, Polyquaternium-6, Polyquaternium-7, Polyquaternium-10, Polyquaternium-11, Polyquaternium-22, Polyquaternium-24, Polyquaternium-37, Polyquaternium-39 and Polyquaternium-100.

According to an embodiment, the inorganic particle may be at least one selected from the group consisting of $TiO_2$, ZnO, iron oxide, mica, sericite, volcanic ash, silica and mud.

According to an embodiment, the inorganic particle may be $TiO_2$.

According to an embodiment, the inorganic particle may be at least one of volcanic ash and silica.

According to an embodiment, the porous composite powder for adsorption of fine dust may include 3-60 wt % of a biodegradable polymer, 0.1-10 wt % of a cationic polymer and 35-90 wt % of inorganic particles, based on the total weight of the porous composite powder.

For example, the content of the biodegradable polymer may be 3 wt % or more, 5 wt % or more, 10 wt % or more, 15 wt % or more, 20 wt % or more, 25 wt % or more, 30 wt % or more, 35 wt % or more, 40 wt % or more, 45 wt % or more, or 50 wt % or more, and 60 wt % or less, 55 wt % or less, 50 wt % or less, 45 wt % or less, 40 wt % or less, 35 wt % or less, 30 wt % or less, or 25 wt % or less, based on the total weight of the porous composite powder.

When the content of the biodegradable polymer is less than 3 wt %, the inorganic particles are present in a relatively excessive amount, and thus the biodegradable polymer cannot function as a bond or a binder for the inorganic particles, thereby making it difficult to form composite powder particles having a porous structure. In addition, when the content of the biodegradable polymer is larger than 60 wt %, the proportion of the inorganic particles is reduced to cause excessive shrinking during the formation of the particles, resulting in deformation of the particles. Therefore, it is possible to form composite powder particles having a porous structure within the above-defined range.

For example, the content of the cationic polymer may be 0.1 wt % or more, 0.5 wt % or more, 1 wt % or more, 1.5 wt % or more, 2 wt % or more, 2.5 wt % or more, 3 wt % or more, 3.5 wt % or more, 4 wt % or more, 4.5 wt % or more, or 5 wt % or more, and 10 wt % or less, 9.5 wt % or less, 9 wt % or less, 8.5 wt % or less, 8 wt % or less, 7.5 wt % or less, 7 wt % or less, 6.5 wt % or less, 6 wt % or less, 5.5 wt % or less, or 5 wt % or less, based on the total weight of the porous composite powder.

When the content of the cationic polymer is less than 0.1 wt %, it is not possible to impart sufficient cationic property, and the effect of adsorbing negatively charged fine dust may be degraded due to a low zeta potential value of the porous composite powder. When the content of the cationic polymer is larger than 10 wt %, skin irritation and a seriously bad amine odor may be generated so that the porous composite powder may not be suitable for cosmetics.

For example, the content of the inorganic particles may be 35 wt % or more, 40 wt % or more, 45 wt % or more, 50 wt % or more, 55 wt % or more, 60 wt % or more, 65 wt % or more, 70 wt % or more, or 75 wt % or more, and 90 wt % or less, 85 wt % or less, 80 wt % or less, 75 wt % or less, 70 wt % or less, 65 wt % or less, 60 wt % or less, 55 wt % or less, 50 wt % or less, or 45 wt % or less, based on the total weight of the porous composite powder.

When the content of the inorganic particles is less than 35 wt %, it is difficult to retain the shape of the porous composite powder. When the content of the inorganic particles is larger than 90 wt %, the content of the biodegradable polymer functioning as a binder is too low to form the particles.

According to an embodiment, the porous composite powder may adsorb fine dust having a particle diameter of 2.5 µm or less. For example, the porous composite powder may adsorb even fine particulate matter having a particle diameter of 2 µm or less, 1.5 µm or less, or 1 µm or less. According to an embodiment of the present disclosure, since the skin pores generally have a size of 30-200 µm or less, the porous composite powder according to an embodiment of the present disclosure can infiltrate into the skin pores, even when fine dust having a small particle diameter infiltrates into the skin pores, and can discharge the negatively charged fine dust, mixed with sebum in the skin pores, out of the skin pores through ionic bonding with ease. Therefore, it is possible to remove harmful substances on the skin with ease upon the cleansing.

In another aspect of the present disclosure, there is provided a composition for adsorption of fine dust including the above-described porous composite powder.

According to an embodiment, the content of the porous composite powder may be 1-30 wt % based on the total weight of the composition. For example, the content of the porous composite powder may be 1 wt % or more, 5 wt % or more, 10 wt % or more, 15 wt % or more, 20 wt % or more, or 25 wt % or more, and 30 wt % or less, 25 wt % or less, 20 wt % or less, 15 wt % or less, 10 wt % or less, or 5 wt % or less, based on the total weight of the composition. When the content is less than 1 wt %, it is not possible to provide a sufficient effect of adsorbing fine dust. When the content is larger than 30 wt %, skin irritation may occur, or a bad odor or a feeling of irritation may be generated. In addition, when the content of the positively charged porous composite powder is increased, the formulation stability may be adversely affected.

According to an embodiment, the composition may be a cosmetic composition, and the appearance of the cosmetic composition may include a cosmetically or dermatologically acceptable medium or base. The formulation may include any formulation suitable for local application. For example, the composition may be provided in the form of a solution, a gel, a solid, a dry slurry product, an emulsion prepared by dispersing an oil phase in an aqueous phase, a suspension, a microemulsion, a microcapsule, a microgranule or an ionic (liposome) and non-ionic sachet dispersant, or provided in the form of cream, skin, lotion, powder, ointment, spray or conceal stick. Such formulations may be obtained by the methods generally known to those skilled in the art. In addition, the cosmetic composition may be used in the form of an aerosol composition further including a compressed propellant.

The cosmetic composition according to an embodiment of the present disclosure is not limited to any particular formulation. For example, the cosmetic composition may be formulated into cosmetic products, such as skin softener, skin astringent, skin nutrient, nutrient cream, massage cream, essence, eye cream, eye essence, cleansing cream, cleansing foam, cleansing water, cleansing tissue including the cosmetic composition, pack, powder, body lotion, body cream, body oil and body essence.

When the formulation is paste, cream or gel, carrier ingredients that may be used include animal fibers, vegetable fibers, wax, paraffin, starch, tragacanth, cellulose derivatives, polyethylene glycol, silicone, bentonite, silica, talc or zinc oxide.

When the formulation is powder or spray, carrier ingredients that may be used include lactose, talc, silica, aluminum hydroxide, calcium silicate or polyamide powder. Particularly, in the case of spray, it may further include a propellent, such as chlorofluorohydrocarbon, propane/butane or dimethyl ether.

When the formulation is a solution or an emulsion, carrier ingredients that may be used include a solvent, a solvating agent or an emulsifying agent, such as water, ethanol, isopropanol, ethyl carbonate, ethyl acetate, benzyl alcohol, benzyl benzoate, propylene glycol, 1,3-butylglycol oil, glycerol fatty acid ester, polyethylene glycol or sorbitan fatty acid ester.

When the formulation is a suspension, carrier ingredients that may be used include a liquid diluent, such as water, ethanol or propylene glycol, a to suspending agent, such as ethoxylated isostearyl alcohol, polyoxyethylene sorbitol ester or polyoxyethylene sorbitan ester, microcrystalline cellulose, aluminum metahydroxide, bentonite, agar, tragacanth, or the like.

When the formulation is a surfactant-containing cleanser, carrier ingredients that may be used include aliphatic alcohol sulfate, aliphatic alcohol ether sulfate, sulfosuccinic acid monoester, isethionate, imidazolinium derivative, methyl taurate, sarcosinate, fatty acid amide ether sulfate, alkylamidobetaine, aliphatic alcohol, fatty acid glyceride, fatty acid diethanolamine, vegetable oil, lanoline derivative, ethoxylated glycerol fatty acid ester, or the like.

The cosmetic composition according to an embodiment of the present disclosure may further include functional additives and other ingredients used currently in a cosmetic composition, besides the active ingredient. The functional additive may include an ingredient selected from the group consisting of water soluble vitamins, oil soluble vitamins, polymer peptides, polymer polysaccharides, spingolipids and seaweed extract.

In addition to the above-mentioned functional additives, the cosmetic composition according to an embodiment of the present disclosure may further include ingredients used conventionally in a cosmetic composition, if necessary, in combination with the functional additives. Such ingredients include an oil and fat ingredient, a moisturizing agent, an emollient, a surfactant, an organic and inorganic pigment, an organic powder, a UV absorbing agent, a preservative, a sterilizing agent, an antioxidant, a plant extract, a pH modifier, an alcohol, a colorant, a fragrance, a blood flow-stimulating agent, a coolant, an anti-perspirant, a purified water, or the like.

According to an embodiment, the cosmetic composition may be at least one selected from the group consisting of cleansing cream, cleansing foam and cleansing water.

Method for Preparing Porous Composite Powder for Adsorption of Fine Dust

In still another aspect of the present disclosure, there is provided a method for preparing the porous composite powder for adsorption of fine dust, including the steps of: preparing a solution including a biodegradable polymer and a cationic polymer; dispersing inorganic particles into the solution including a biodegradable polymer and a cationic polymer; and spray drying the solution including the inorganic particles dispersed therein.

Particularly, referring to FIG. 1, the biodegradable polymer and the cationic polymer are dissolved in an organic solvent to prepare a solution containing the biodegradable polymer, the inorganic particles are introduced to the solution and may be dispersed by using a homogenizer. Then, the solution containing the inorganic particles dispersed therein is spray dried by using a nozzle to obtain porous composite powder for adsorption of fine dust.

According to an embodiment of the present disclosure, the cationic polymer may be dissolved in the solution together with the biodegradable polymer, and the inorganic particles may be dispersed homogeneously in the solution. When the cationic polymer is dissolved in a solvent together with the biodegradable polymer, it is possible to form porous composite powder in which the cationic polymer is entangled with (forming a composite with) the polymer chains, while the cationic polymer is settled together with the biodegradable polymer during the subsequent spraying.

As a result, it is possible to obtain porous composite powder, which includes the cationic polymer forming a composite with the biodegradable polymer inside of the biodegradable polymer and/or on the surface thereof and the inorganic particles incorporated homogeneously thereto, with ease by using a spray drying process.

Herein, the humidity inside of the spray drier may be maintained at 30% or more, the temperature therein may be maintained at room temperature, and spray drying may be carried out at a feed rate of 20% with an aspirator level of 70% under 20 atm.

According to an embodiment, during the spray drying, the solution containing the inorganic particles dispersed therein may be agitated in a container, before introduction to a pump, which prevents the inorganic particles from being settled before the spray drying.

According to an embodiment, the solvent of the solution containing the biodegradable polymer and cationic polymer may be at least one selected from the group consisting of anhydrous dichloromethane, ethanol and acetone, preferably anhydrous dichloromethane.

According to an embodiment, after the step of spray drying, the method may further include a washing and drying step. For example, the method may further include a step of washing the product with methanol and drying the to product on a tray. In this manner, it is possible to obtain porous composite powder from which the residual solvent is removed completely.

In still another aspect of the present disclosure, there is provided a method for adsorption of fine dust, which includes applying the above-described porous composite powder to the skin.

In still another aspect of the present disclosure, there is provided a method for adsorption of fine dust, which includes applying the above-described composition including the porous composite powder to the skin.

In still another aspect of the present disclosure, there is provided use of the porous composite powder for the preparation of a composition for adsorption of fine dust.

In yet another aspect of the present disclosure, there is provided use of the above-described porous composite powder for adsorption of fine dust.

Hereinafter, the present disclosure will be explained in more detail with reference to examples. However, the following examples are for illustrative purposes only. In addition, it will be apparent to those skilled in the art that the scope of the present disclosure is not limited to the following examples.

EXAMPLES

Example 1—Preparation of Porous Composite Powder for Adsorption of Fine Dust (AP Sphere-1)

To obtain porous composite powder (AP Sphere) for adsorption of fine dust, polylactic acid-co-glycolic acid (PLGA, available from GALACTIC), titanium dioxide (TiO$_2$, available from Daito Kase, OTS-2 TiO$_2$ CR-50), Polyquaternium-10 (PQ10, available from Dow Chemical, Ucare polymer JR-30) as a cationic polymer, and anhydrous dichloromethane (DCM, available from Sigma-Aldrich, purity >99.8%) were prepared.

Then, the spray drying device as shown in FIG. 1 was used to obtain porous composite powder (also referred to as AP Sphere-1, hereinafter) for adsorption of fine dust according to the following process.

[Spray Drying Process]

1) 45 g of PLGA and 5 g of PQ10 are dissolved in 1 L of DCM as a solvent.

2) 50 g of TiO$_2$ is introduced to the solution and dispersed therein by using a homogenizer.

3) The resultant dispersion is spray dried.

4) The internal humidity of the spray dryer is maintained at 30% or more, and the internal temperature thereof is maintained at room temperature.

5) The spray drying is carried out at a feed rate of 20% with an aspirator level of 70% under 20 atm. The dispersion is agitated continuously with an agitator.

6) The spray dried composite powder is dried to remove the residual solvent completely.

Figure 2A:
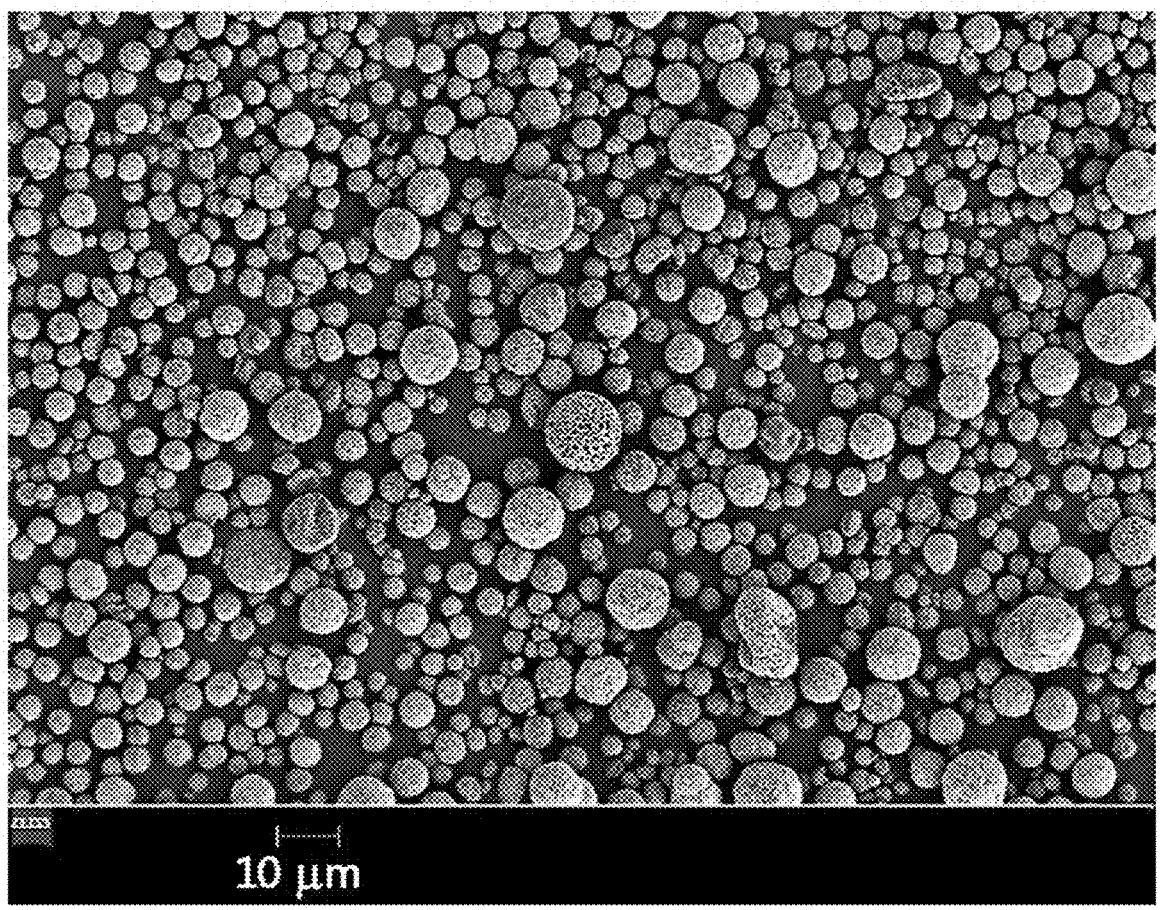
FIG. 2A and FIG. 2B show electron microscopic images of the porous composite powder according to an embodiment of the present disclosure.
Figure 2B:
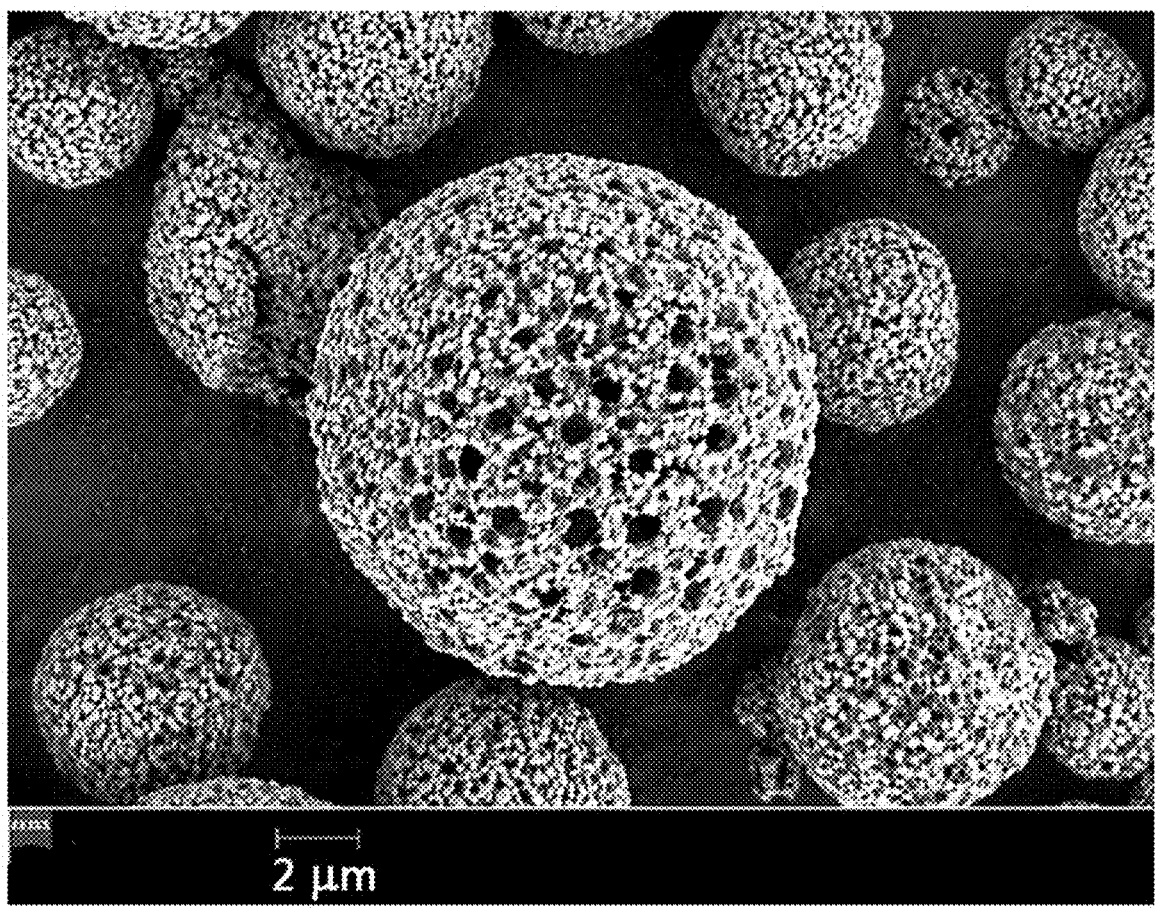

As shown in FIG. 2A and FIG. 2B, it is possible to incorporate TiO$_2$ successfully into the porous polymer. It can be seen from the surface images that the composite powder is impregnated compactly with TiO$_2$ particles, while including pores having a size of several hundreds of nanometers. Particularly, the porous composite powder has a size of about 10-50 μm (micrometer) and a pore size of about 10 nm to 1 μm.

Test Example 1—Determination of Zeta Potential of Porous Composite Powder

The porous composite powder (PLGA:T102:PQ10=45: 50:5) according to Example 1, and as a control, porous composite powder (PLGA:T102:PQ10=50:50:0) prepared in the same manner as Example 1, except that no cationic polymer was used, were determined in terms of surface charges. Aqueous solution containing 0.01 wt % of a sample was prepared in a quartz cuvette, and 100 μL of the solution was loaded to measure the zeta potential by using Zetasizer Nano ZS (available from Malvern).

Figure 3:
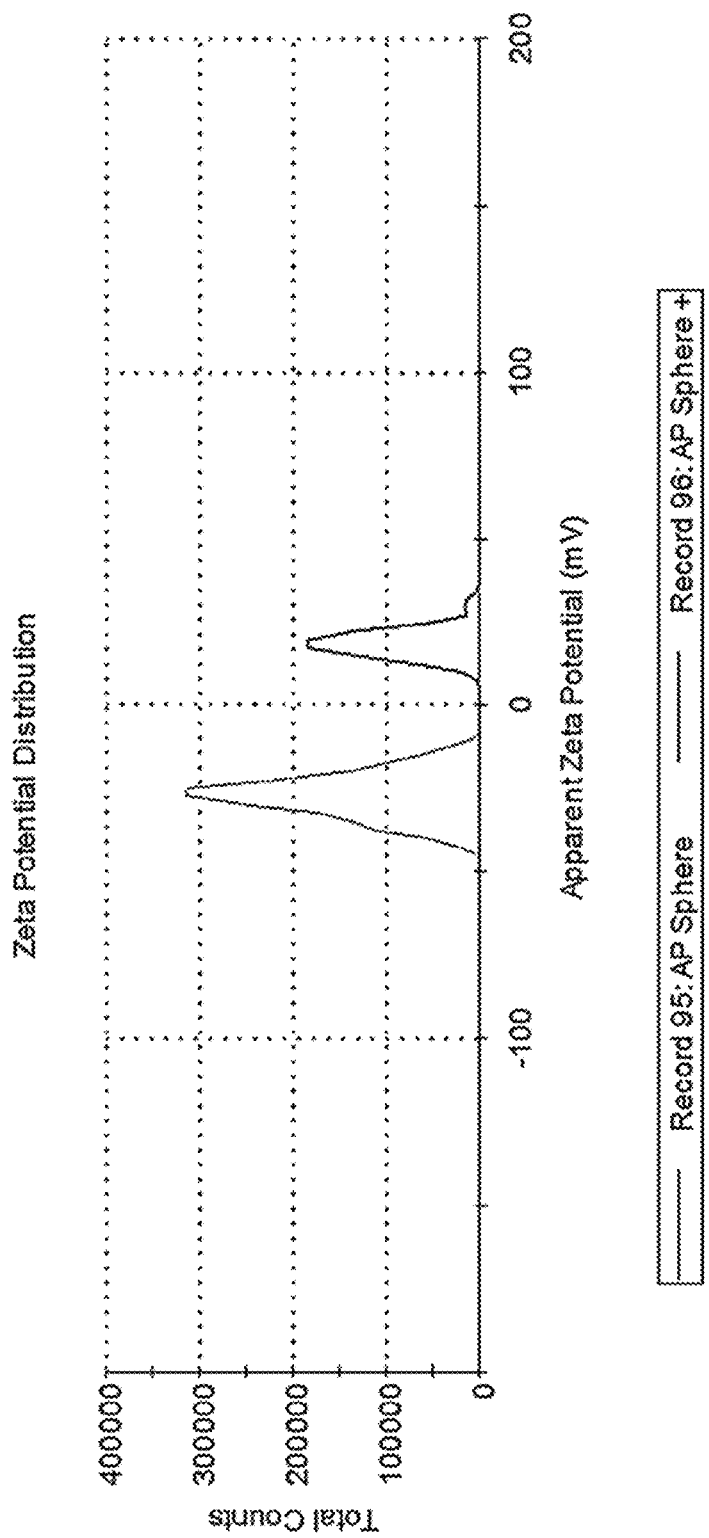
FIG. 3 shows the result of determination of zeta potential of the porous composite powder according to an embodiment of the present disclosure.

Referring to FIG. 3, it can be seen that the surface charges of AP Sphere-1 are converted into cationic charges (+18.9 mV) (Record 96: AP Sphere+) from negative charges (−26.8 mV) (Record 95: AP Sphere) due to the addition of cation.

Test Example 2—Evaluation of Oil Absorption

Figure 4:
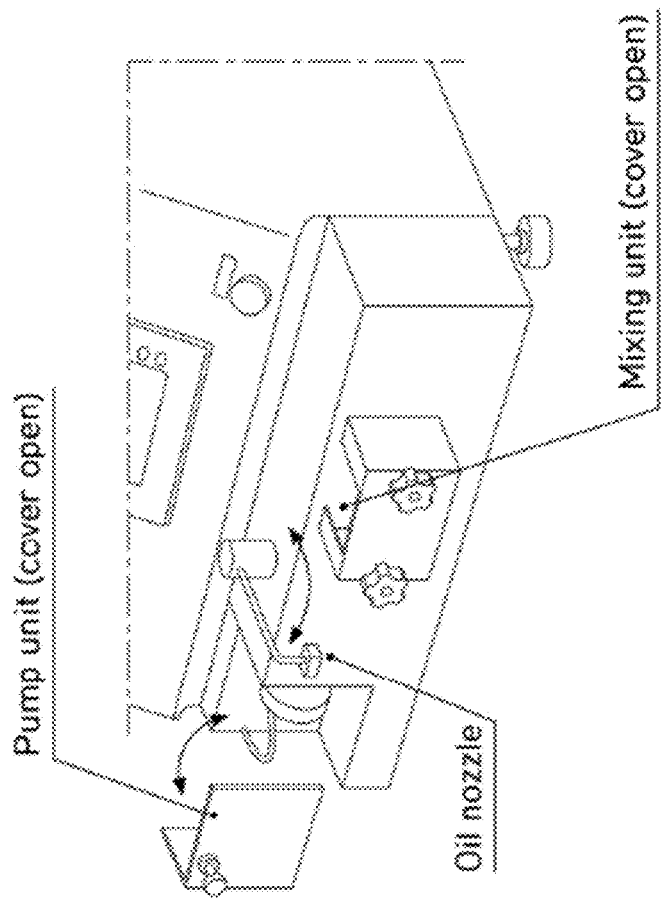
FIG. 4 shows the oil absorption measuring system (S-500, Asahi Souken) used according to an embodiment of the present disclosure.
Figure 4:
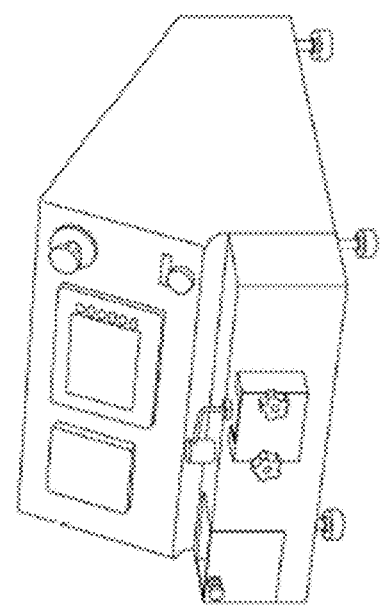
Figure 5:
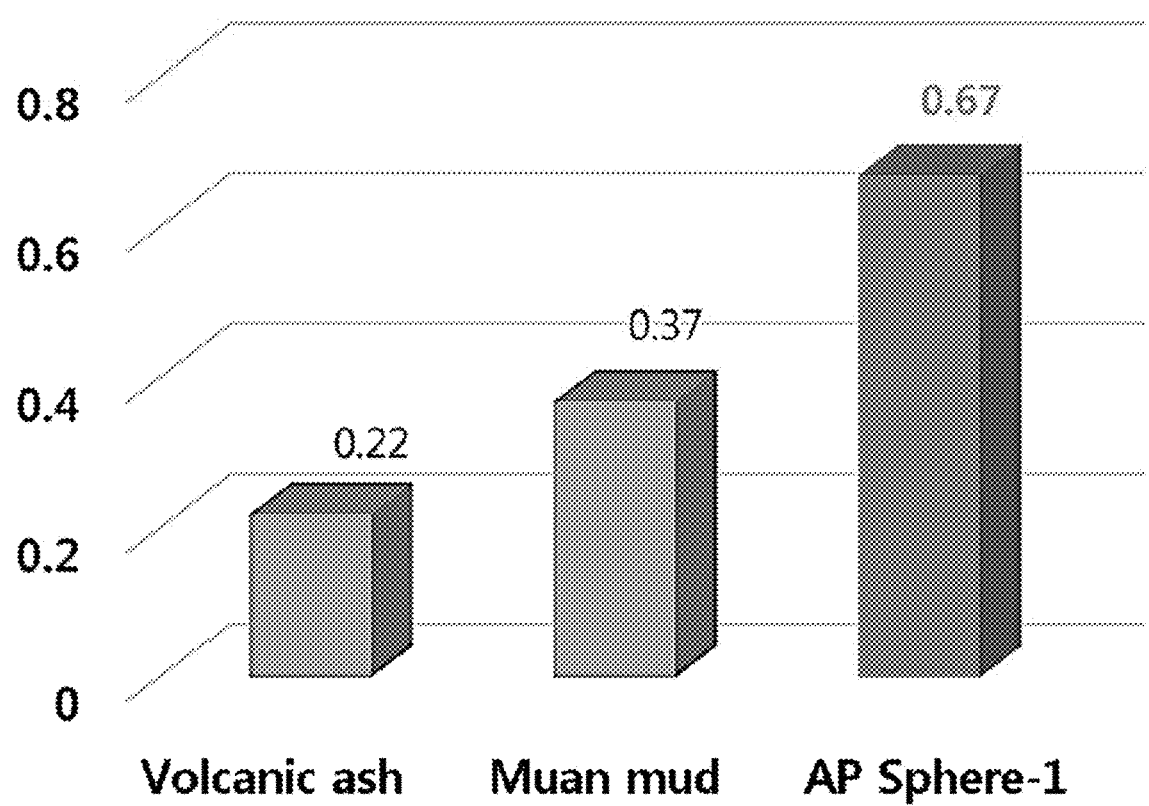
FIG. 5 shows the result of determination of oil absorption (mL/g) of the porous composite powder according to an embodiment of the present disclosure.

To determine whether AP Sphere-1 can effectively adsorb sebum containing fine particulate matter into the pores or not, the oil absorption for MCT oil (CAS No. 73398-61-5) having the most similar physical properties to the physical properties of sebum was evaluated according to the following method by using a commercially available oil absorption measuring device (S-500, Asahi Souken, FIG. 4). The results are shown in FIG. 5.

[Test Method]

1) The weight of powder to be tested is measured and the powder is introduced to a sample chamber.

2) When the operation of the device is started, oil is added dropwise into the chamber by an oil pump, and two mixers are rotated to carry out kneading of the powder with oil.

3) As the amount of the oil introduced to the chamber is increased, the torque value applied to the mixers is increased, and then the test is finished, when the torque value reaches the highest value.

4) Herein, the amount (mL) of oil corresponding to 70% of the highest torque is divided by the amount (g) of the sample, and the calculated value is taken as the oil absorption (mL/g) of the powder.

As controls, volcanic ash (INCI name) and Muan mud (INCI name: sea silt), which are adsorptive materials used frequently in the conventional mask pack products, or the like, were used. As shown in FIG. 5, AP Sphere-1 shows an oil absorption 2-3 times higher than the oil absorption of the conventional adsorptive materials. This suggests that AP Sphere-1 can adsorb fine particulate matter contained in sebum in a significantly larger amount, and can capture fine particulate matter into the pores, and thus shows a higher effect of isolating harmful fine particulate matter from the skin.

Test Example 3—Evaluation of Zeta Potential and Adsorption Capability

To evaluate the fine particulate matter adsorption performance of AP Sphere-1 (FIG. 6G), cellulose particles (Comprecel, FIG. 6A) as a scrubbing agent, three types of silica (Neosil, FIG. 6B/Spherica P-1500, FIG. 6C/Lucidsil, FIG. 6D), spherical PMMA particles (Art Pearl, FIG. 6E), and porous PMMA particles (Sunpmma coco-170, FIG. 6F), each having a different zeta potential, were used as controls.

Figure 6A:
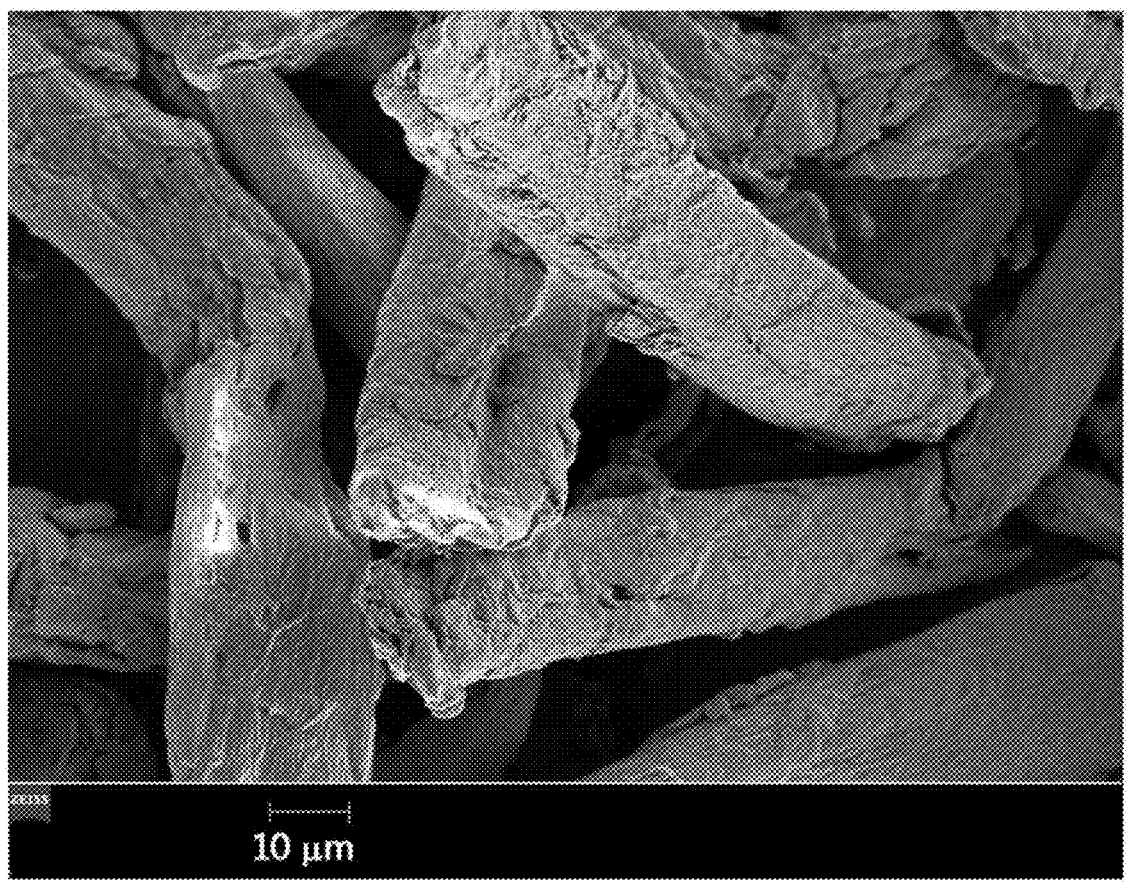
FIG. 6A to FIG. 6G show scanning electron microscopic (SEM) images and the results of zeta potential measurement of the porous composite powder according to an embodiment of the present disclosure and the controls.
Figure 6B:
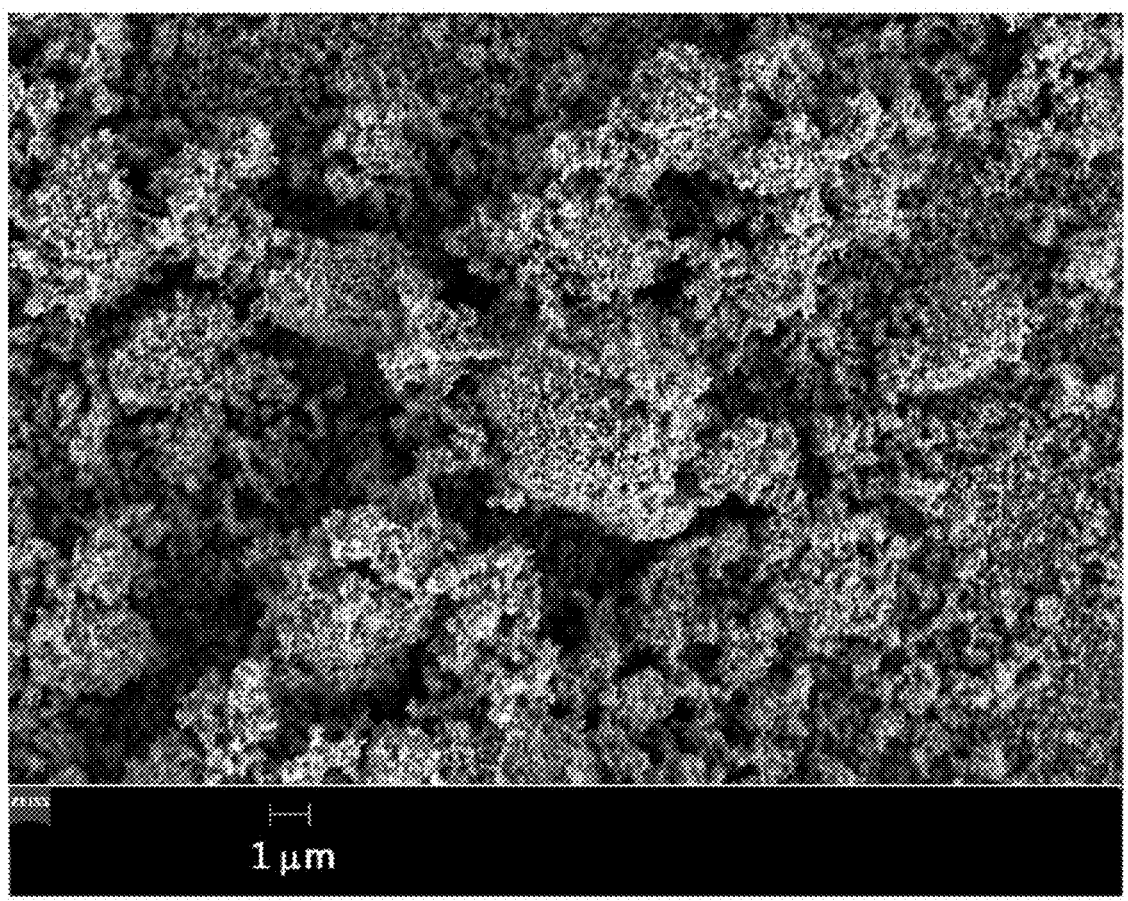
Figure 6C:
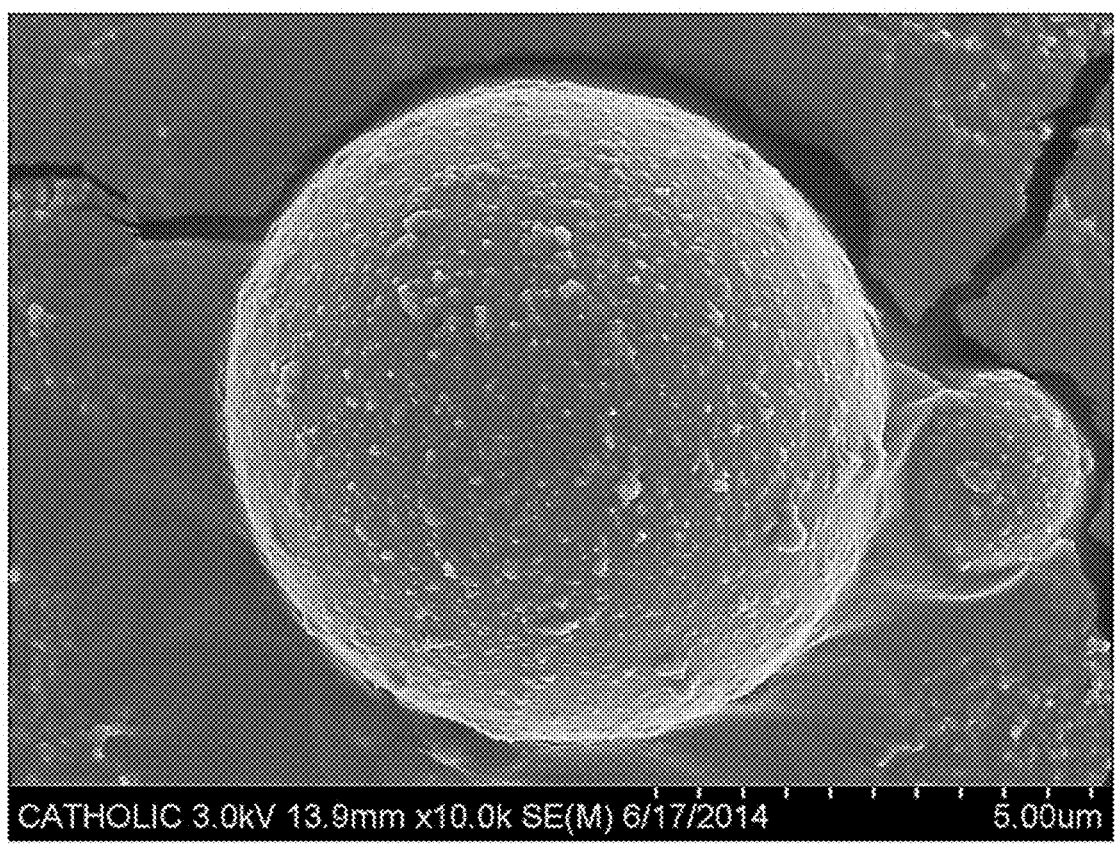
Figure 6D:
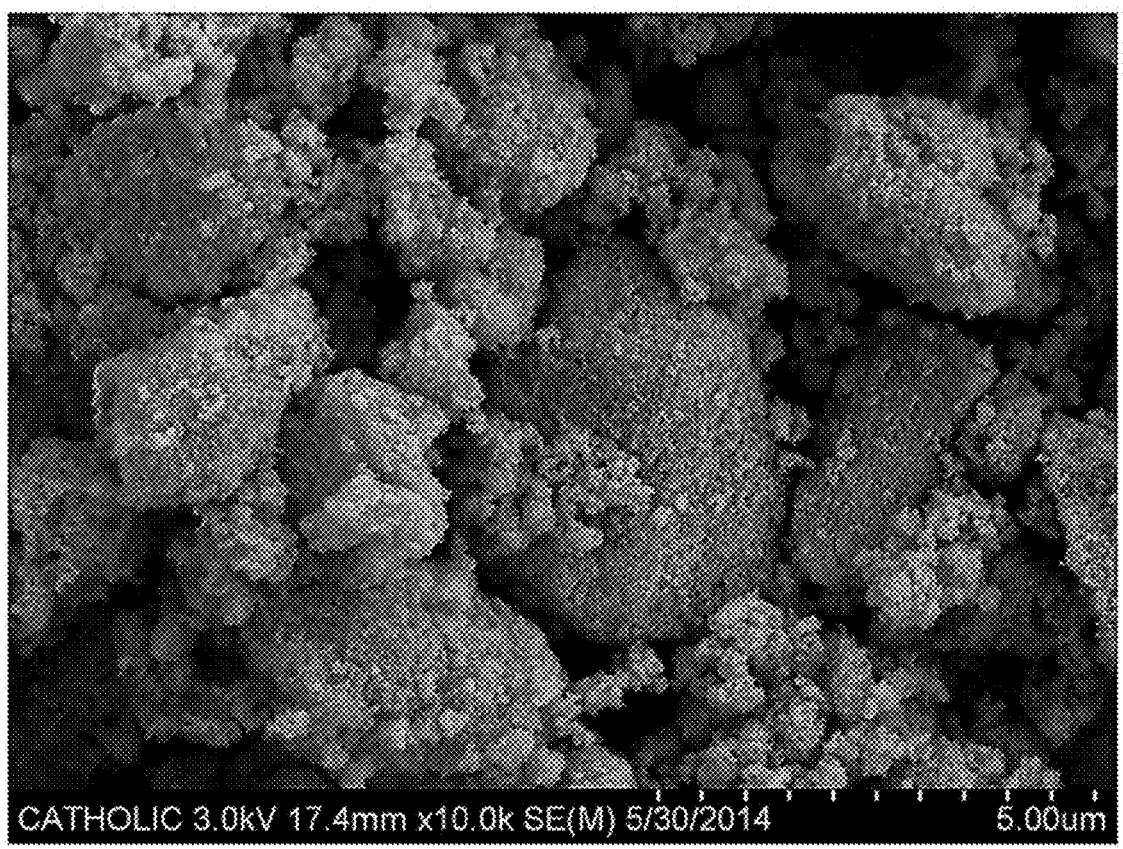
Figure 6E:
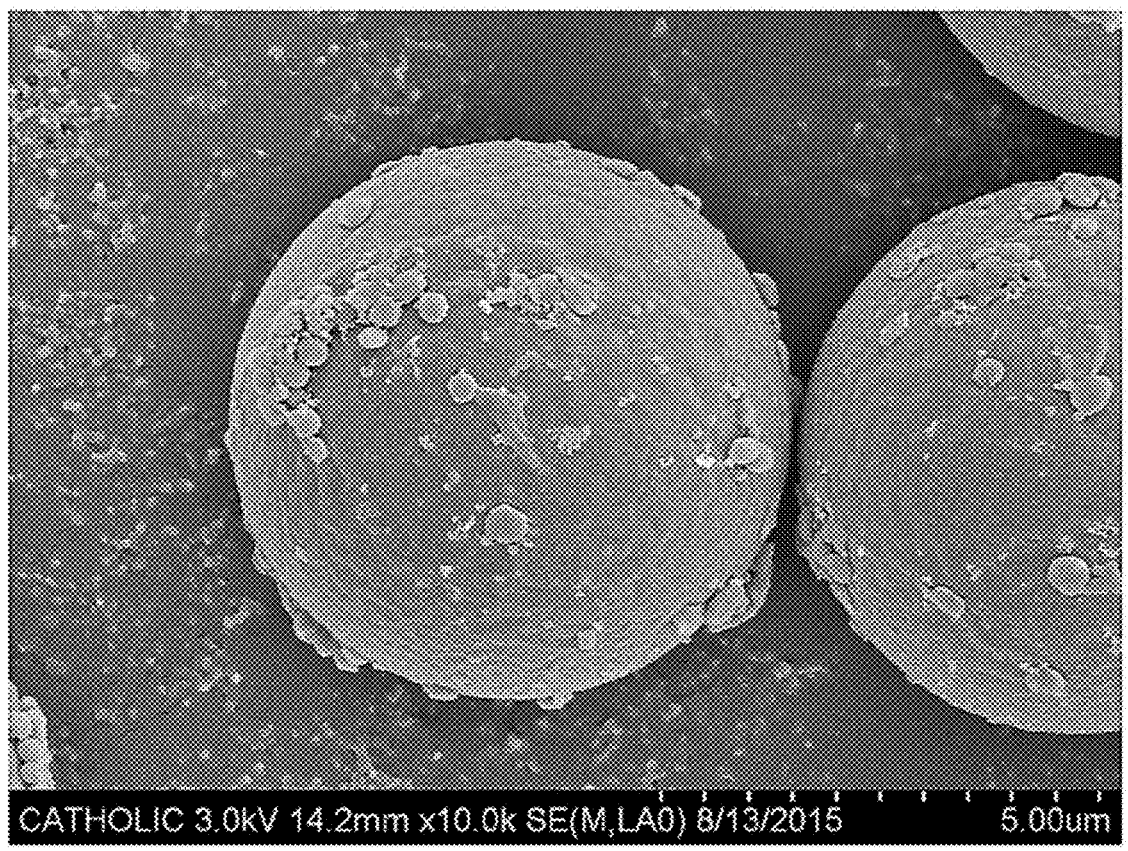
Figure 6F:
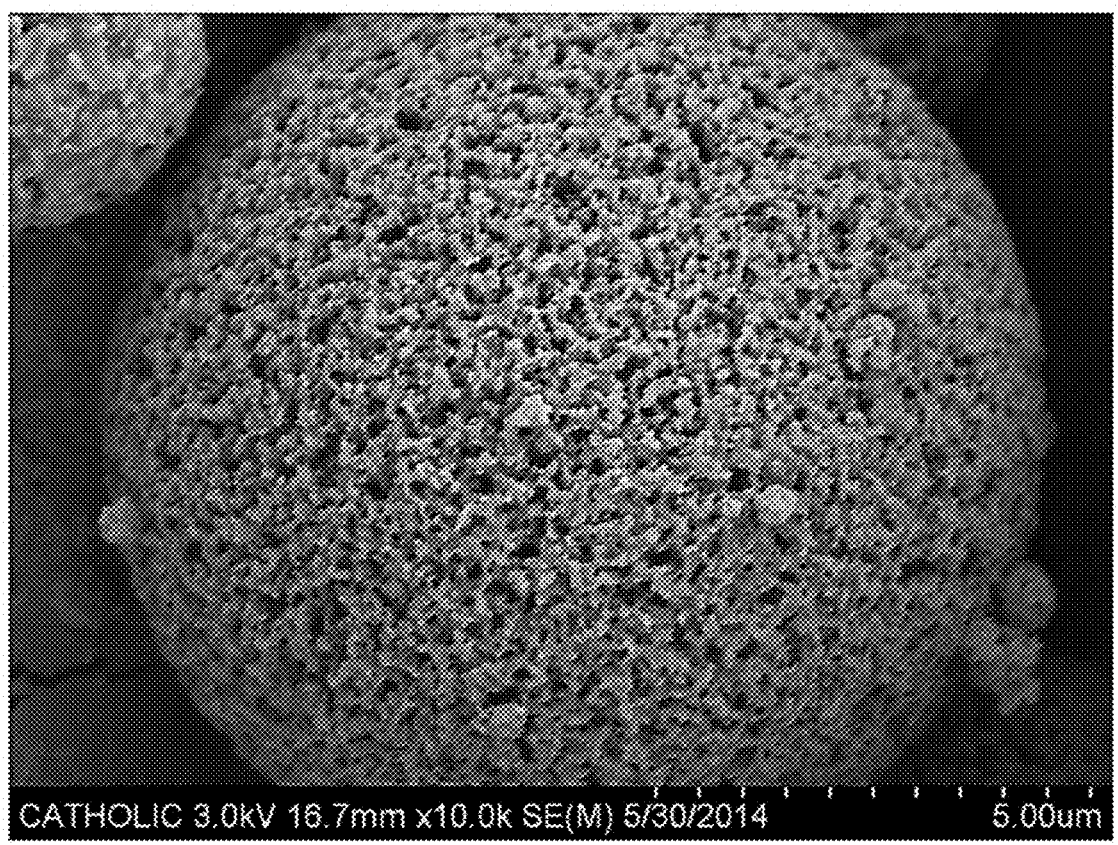
Figure 6G:
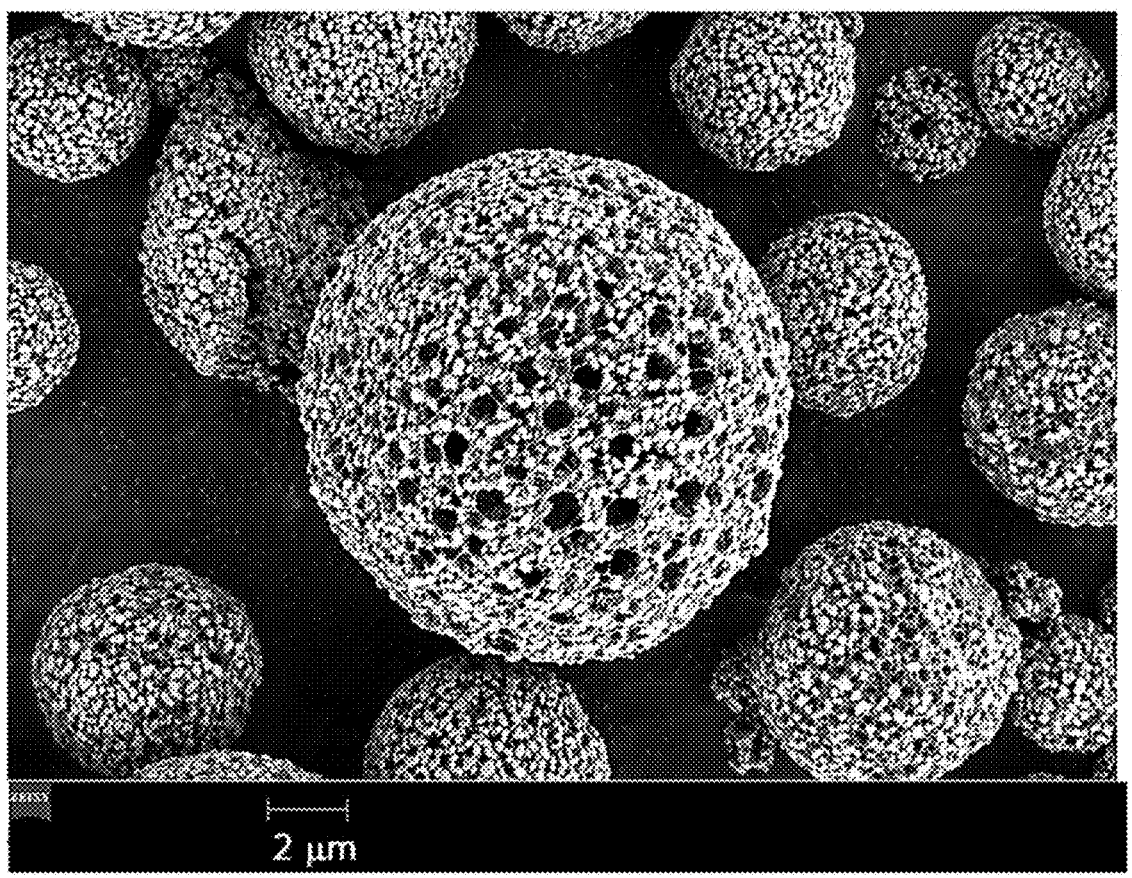

First, the zeta potential of each of the controls as shown in FIG. 6A to FIG. 6F was determined as follows: FIG. 6A: Comprecel (−20.7 mV), FIG. 6B: Neosil (−21.3 mV), FIG. 6C: Spherica P-1500 (−15.5 mV), FIG. 6D: Lucidsil (−13.0 mV), FIG. 6E: Art Pearl K-7 (−29.7 mV), and FIG. 6F: Sunpmma coco-170 (−20.8 mV). Therefore, it can be seen that all of the particles of the controls are negatively (−) charged. On the contrary, it can be seen that the zeta potential of AP Sphere-1 (FIG. 6G) is +18.9 mV.

Then, the adsorption capability was evaluated according to the following test method.

[Test Method]

1) 1 mg of standard fine particulate matter (SRM 1650b) is dispersed in 10 g of ethanol by using ultrasonic waves.

2) 500 mg of powder to be tested is introduced to the dispersion, the dispersion is agitated with a magnetic stirrer for 5 minutes, and is allowed to stand.

3) Filtering is carried out by using filter paper and the color of the filtrate is observed.

4) The transmittance is determined by using a turbidimeter.

After evaluating the adsorption capability, adsorption occurs, after powder particles are introduced to the solution containing standard fine particulate matter (SRM 1650b) dispersed therein and the dispersion is agitated. Herein, even when agitation is stopped and the dispersion is allowed to stand for a long time, light powder particles are not settled but float in the dispersion. Under this condition, it is difficult to compare different powder particles with each other in terms of fine particulate matter adsorption performance.

Herein, filtering with filter paper totally removes fine dust adsorbed on the powder and leaves non-adsorbed fine particulate matter alone. Then, quantitative comparison of fine particulate matter adsorption capability may be performed by measuring the transmittance of the filtrate.

Figure 7A:
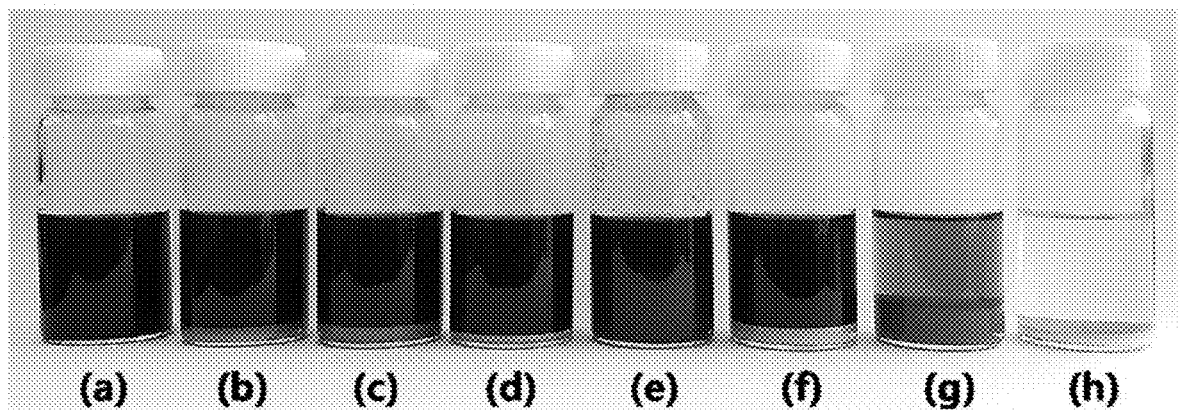
FIG. 7A and FIG. 7B show the results of determination of fine particulate matter adsorption performance of the porous composite powder according to an embodiment of the present disclosure and the controls.
Figure 7B:
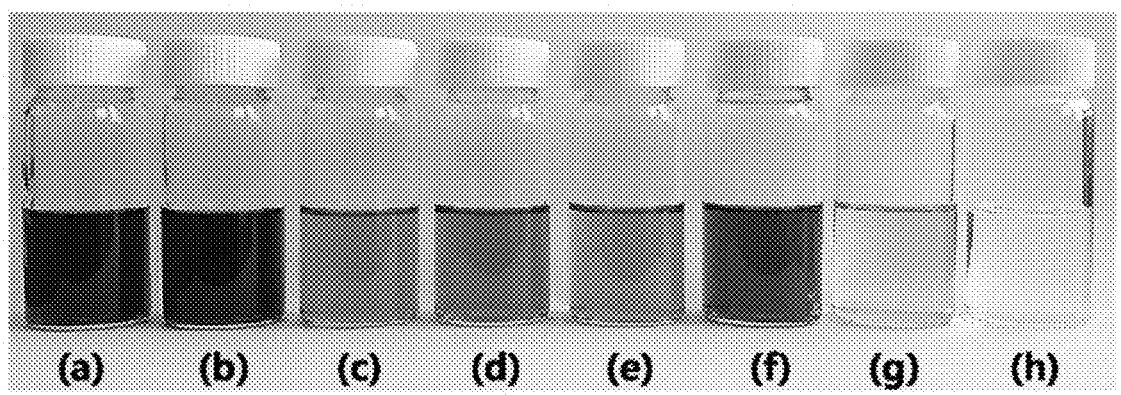
Figure 8A:
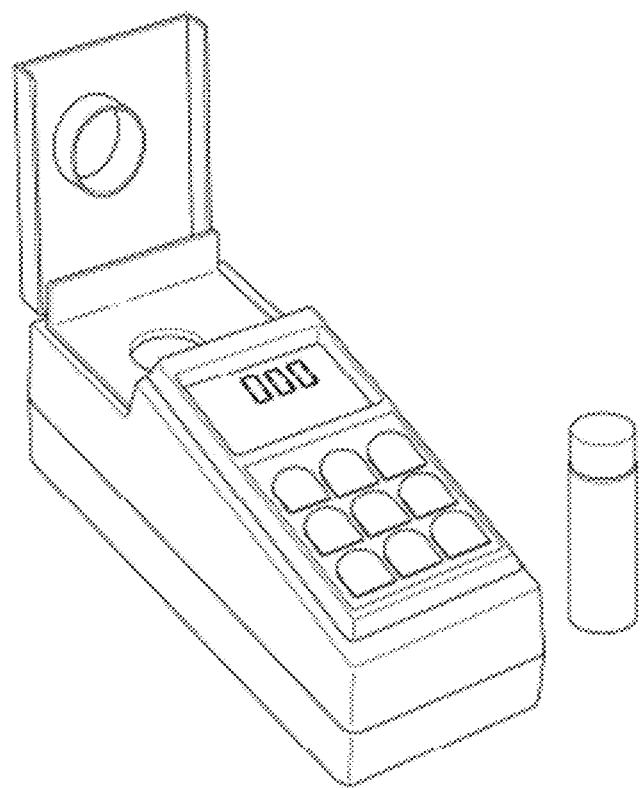
FIG. 8A illustrates an instrument for determining transmittance.
Figure 8B:
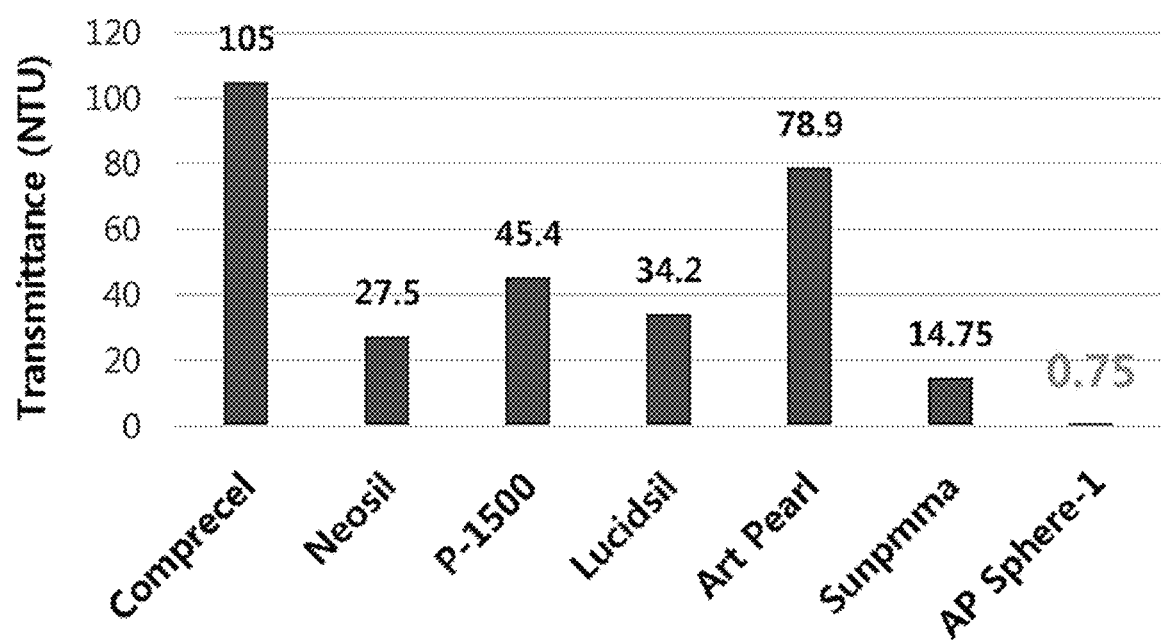
FIG. 8B shows the results of determination of transmittance of the porous composite powder according to an embodiment of the present disclosure and the controls.

The test results are shown in FIG. 7A, FIG. 7B and FIG. 8B. In FIG. 7A and FIG. 7B, the samples correspond to the non-treated sample (a), cellulose particles (Comprecel) (b), three types of silica (Neosil (c)/Spherica P-1500 (d)/Lucidsil (e)), spherical PMMA particles (Art Pearl, (f)), porous PMMA particles (Sunpmma coco-170, (g)), and AP Sphere-1 (h), in turn, from the left side.

After the test, as shown in FIG. 7A, the negatively charged control powder particles cannot cause settling of fine particulate matter, and thus the dispersion shows a black color, while only the porous polymer, i.e. Sunpmma particles (g) partially causes settling so that the color of the dispersion may become slightly pale. On the contrary, when introducing AP Sphere-1 (h), most fine particulate matter is adsorbed/settled so that the dispersion may become significantly transparent. AP Sphere-1 (h) includes 50% or more of $TiO_2$ functioning as a support, and thus it has higher density as compared to silica or PMMA particles and shows higher capability of adsorbing and settling fine particulate matter (FIG. 7A).

Then, the samples are filtered with filter paper and the filtrates are observed. It can be seen that cellulose powder (Comprecel) (b) shows little change in color even after filtering, suggesting that it has poor fine particulate matter adsorption capability. In the case of the other samples, the color of each dispersion becomes slightly pale after filtering, although there is a difference in degree. In the case of AP Sphere-1 (h), the dispersion becomes substantially transparent after filtering (FIG. 7B).

After measuring the transmittance of each filtrate by using a turbidimeter of FIG. 8A for the purpose of quantitative evaluation, some powder samples are still insufficient for complete removal of fine particulate matter, although they are shown to have fine particulate matter adsorption capability. On the contrary, the filtrate of AP Sphere-1 has a transmittance of 0.75 NTU, which is an excellent level near the domestic standard of edible drinking water (0.5 NTU) (FIG. 8B).

Therefore, it can be seen from the above results that AP Sphere-1, having a porous structure favorable to adsorption, including $TiO_2$ favorable to settling and showing charges converted into cationic charges on the surface and inside of the pores, can adsorb/settle fine particulate matter most effectively through ionic bonding, as demonstrated by visual RTB.

Test Example 4—Evaluation of Adsorption Capability Depending on Cationic Polymer (PQ10)

Figure 9:
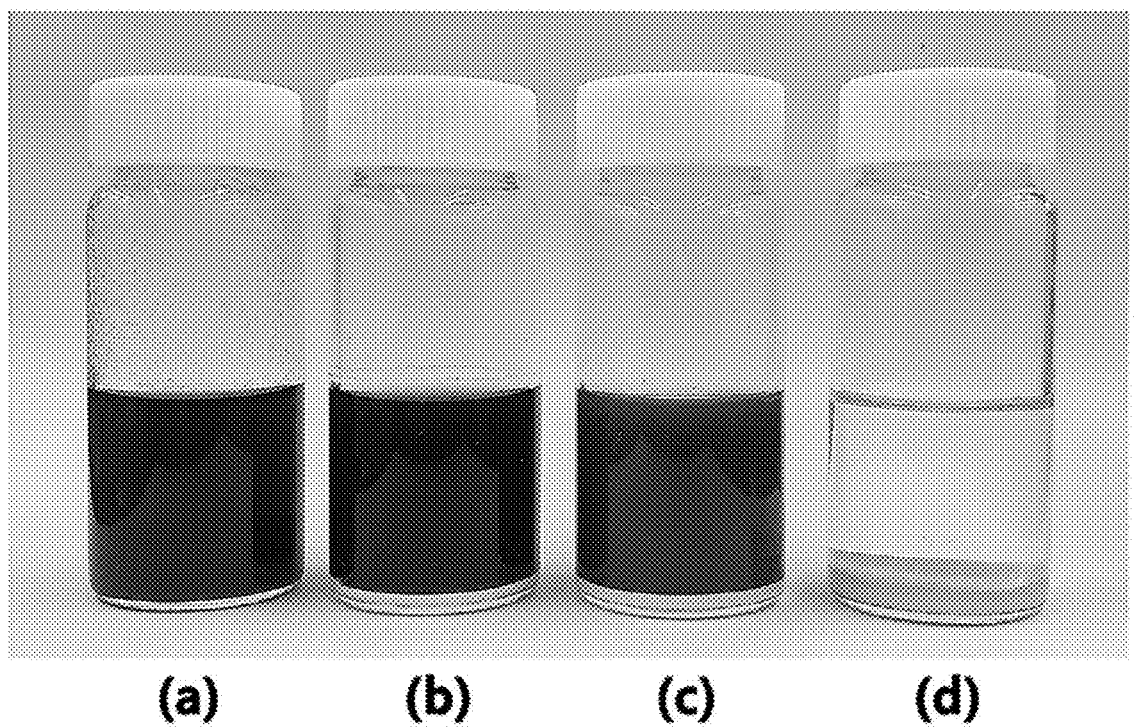
FIG. 9 shows the result of determination of fine particulate matter adsorption performance of the porous composite powder according to an embodiment of the present disclosure.

To analyze the function of a cationic polymer intensively, the following adsorption test was carried out. The test was carried out by using the four samples of dispersion of standard fine particulate matter including: (a) a cationic polymer (PQ10) alone, (b) AP Sphere (no PQ10) alone, (c) AP Sphere (no PQ10) simply in combination with PQ10, and (d) AP Sphere-1 (with PQ10) composite powder alone (FIG. 9).

After the test, when using the cationic polymer (PQ10) alone (a) and AP Sphere (no PQ10) alone (b), there is no effect of adsorbing fine particulate matter. When using AP Sphere (no PQ10) simply in combination with PQ10 (c), there is little effect of adsorbing fine particulate matter. On the contrary, it is shown that when using the cation-bound AP Sphere-1 (with PQ10) composite powder (d), it is possible to obtain an excellent effect of adsorbing and settling fine particulate matter.

Test Example 5—Column Passing Test

To determine the mechanism of adsorption of fine particulate matter to AP Sphere-1 more visually, AP Sphere-1 was packed in a column, an fine particulate matter dispersion was loaded thereto, and then the color of the eluent passed from the column was observed. The test result is provided divisionally at the start point (a), the mid-point (b) and the finish point (c).

Figure 10:
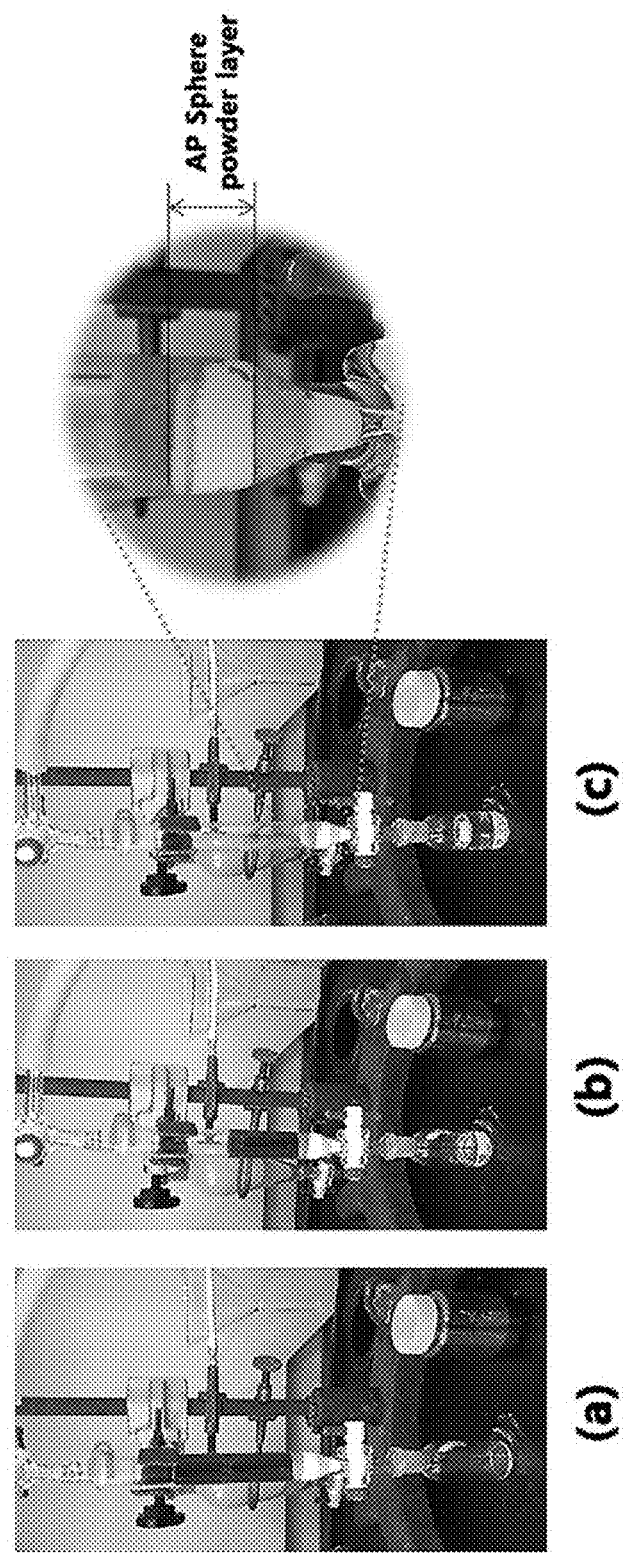
FIG. 10 shows the result of the column passing test of the porous composite powder according to an embodiment of the present disclosure.

After the test, a black colored layer was observed, while fine particulate matter was adsorbed to the layer packed with AP Sphere, and the eluent at each time point was transparent (FIG. 10).

Test Example 6—AP PM2.5 Adsorption Test

An adsorption test was carried out by using fine particulate matter AP PM2.5 actually collected in the rooftop of Amore Pacific Research and Development Center. AP PM 2.5 was captured with a polytetrafluoroethylene (PTFE) filter (Zefluor™ Pall Life Science, Mexico) and extracted through ultrasonication in ethanol for 30 minutes.

Figure 11:
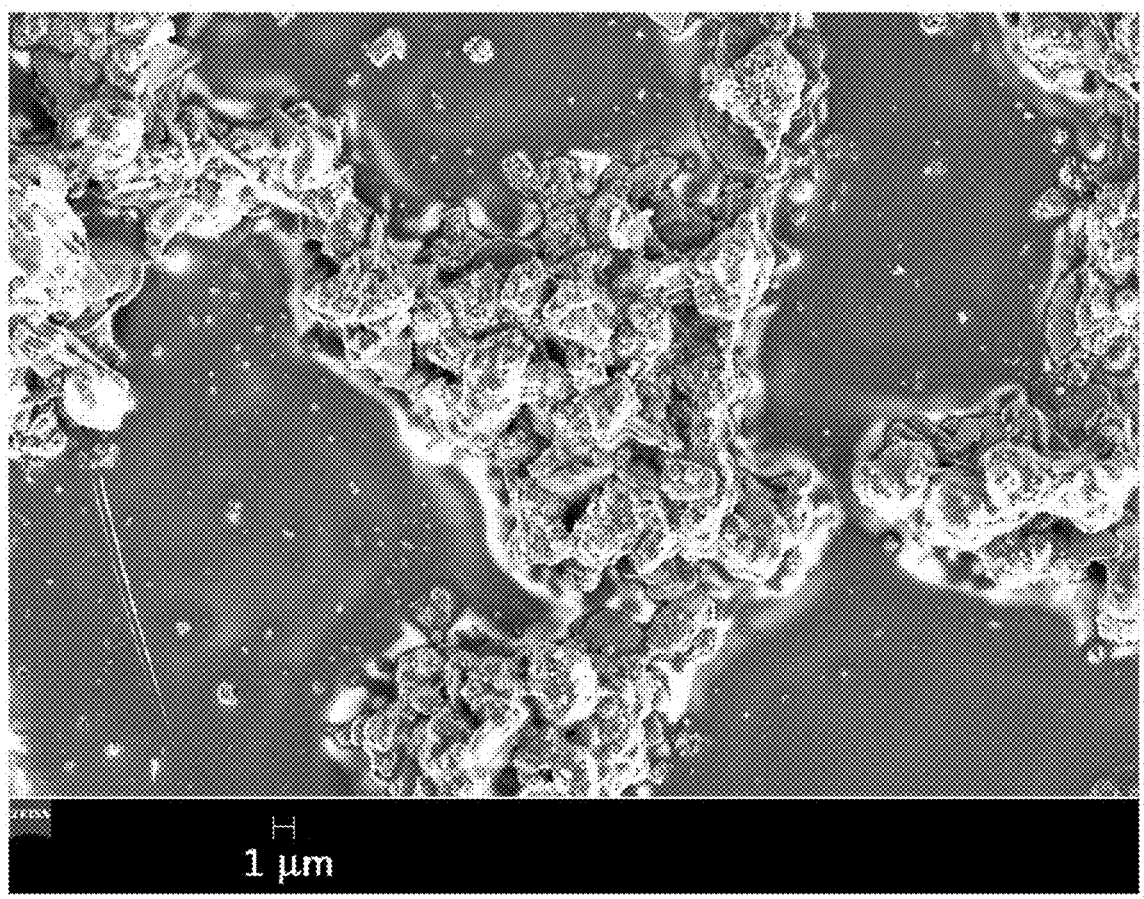
FIG. 11 is an SEM image of AP PM2.5 used according to an embodiment of the present disclosure.

It is shown that AP PM2.5 includes particles with a size of 2.5 μm or less through scanning electron microscopy (SEM) (FIG. 11), contains the top 5 heavy metals (As, Cd, Sb, Pb, Ni) through inductively coupled plasma-mass spectrometry (ICP-MS) (Table 1), and is negatively charged (−11.7 mV) through the determination of zeta potential.

TABLE 1

| Metal ppm | Li 5.8 | Na 3359.0 | Mg 913.3 | Al 2968.9 | K 3010.6 | Ti 126.2 |
|---|---|---|---|---|---|---|
| Metal ppm | Cr 33.0 | Mn 160.5 | Fe 3512.4 | Co 2.0 | Ni 40.0 | Cu 188.5 |
| Metal ppm | Zn 449.6 | Ge 4.2 | As 25.3 | Rb 12.2 | Sr 14.3 | Cd 7.8 |
| Metal ppm | In 171.6 | Sn 23.7 | Sb 101.6 | Cs 1.0 | Ba 116.8 | Pb 167.1 |

Figure 12:
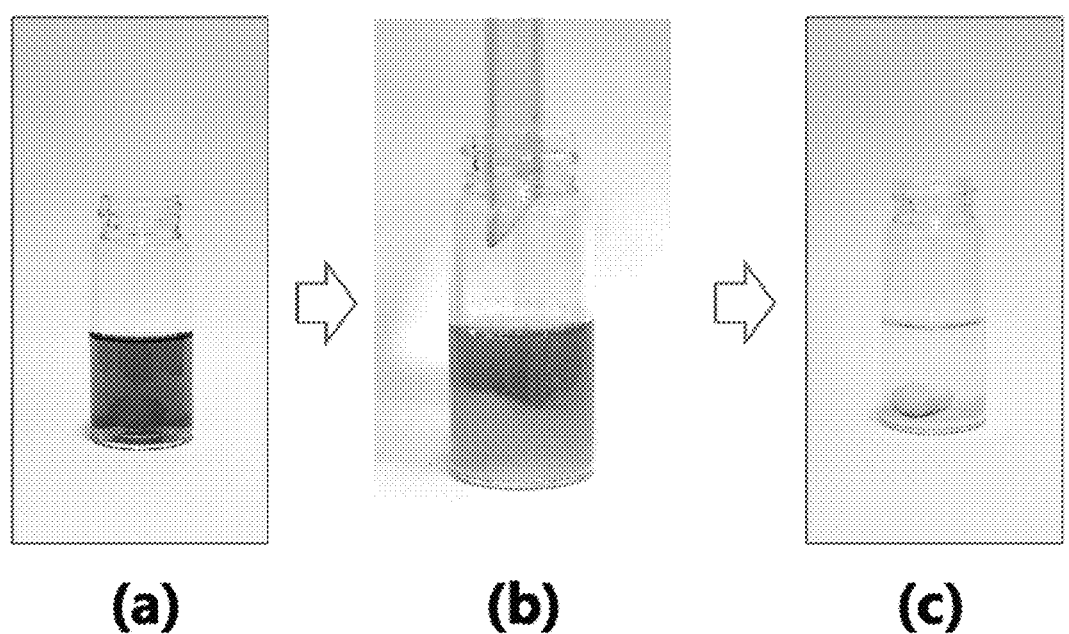
FIG. 12 shows the result of AP PM2.5 adsorption performance of the porous composite powder according to an embodiment of the present disclosure.

The adsorption test results are provided in FIG. 12 divisionally for AP PM 2.5 dispersion (a), after introduction of AP Sphere-1 and agitation (b), and after the lapse of 1 hour (c). Referring to FIG. 12, when AP Sphere-1 is introduced and agitation is started, adsorption of AP PM2.5 is started, while the color is turned into a gray color as a whole. In addition, 1 hour after stopping agitation, fine particulate matter is totally settled to provide a clear state as shown in FIG. 12(c). Therefore, it can be seen that AP Sphere shows the same excellent effect of removing the AP PM2.5 fine particulate matter sample (containing the top 5 heavy metals) collected in the rooftop of Amore Pacific Research and Development Center as well as foreign standard fine particulate matter.

Figure 13A:
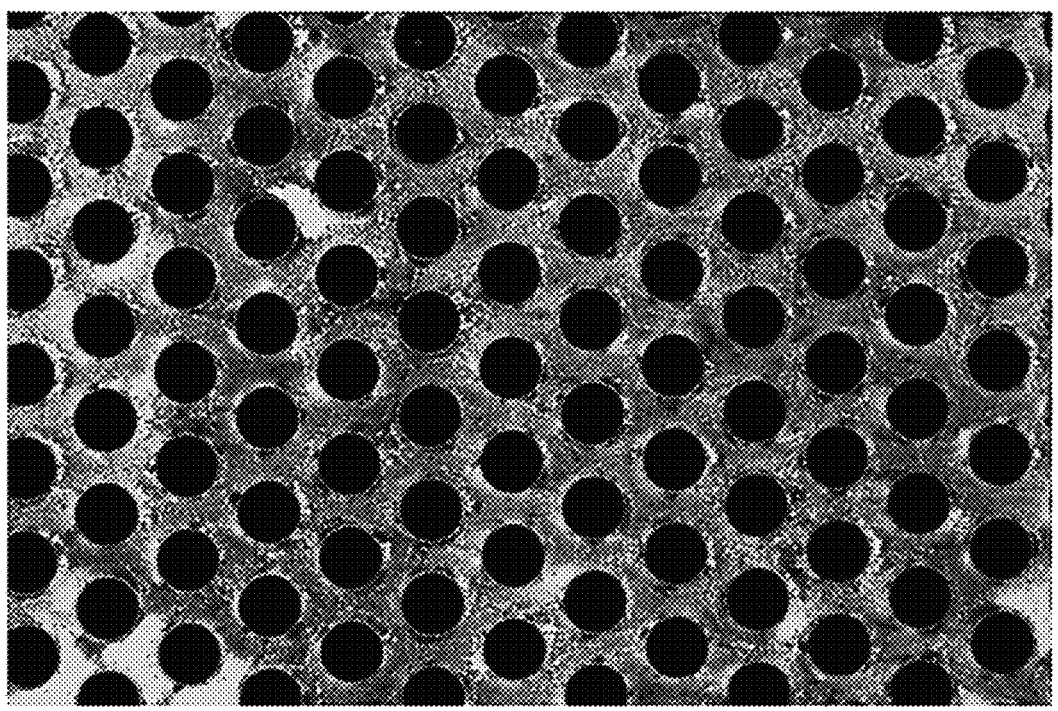
FIG. 13A and FIG. 13B show the results of evaluation of fine particulate matter removing performance using mimetic skin pores of the porous composite powder according to an embodiment of the present disclosure.
Figure 13B:
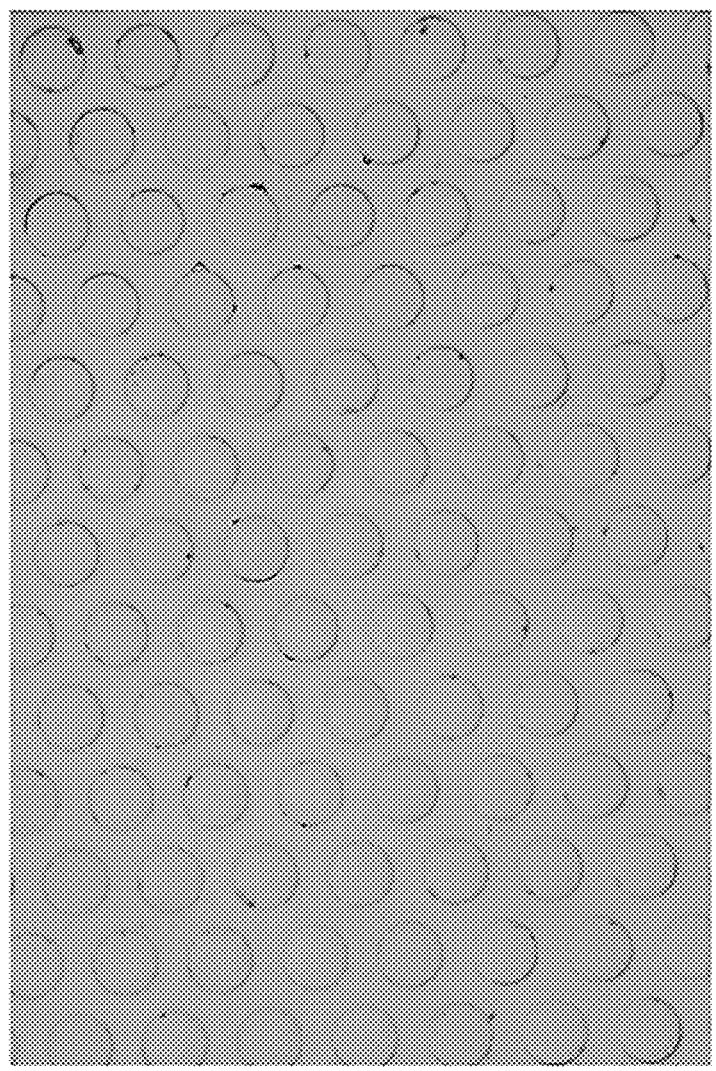

Test Example 7—Evaluation of Effect of Removing Fine Particulate Matter of Foam Cleanser Formulation Based on the earlier patent application, Korean Patent Application No. 10-2017-0154993 (Mimetic skin pores, Method for Evaluating Material Having Skin Cleansing Capability Using the Same, and Method for Screening Material Having Skin Cleansing Capability Using the Same), a cleansing foam formulation containing 5 wt % of AP Sphere-1 was prepared according to the composition of the following Table 2, and the effect of removing fine particulate matter was tested by the following method. The results are shown in FIG. 13A and FIG. 13B.

TABLE 2

| Ingredients | Content (Unit: Wt %) |
|---|---|
| Purified water | 26.85 |
| Disodium EDTA | 0.05 |
| Glycerin | 28 |
| Lauric acid | 3 |
| Myristic acid | 12 |
| Stearic acid | 12 |
| Glyceryl stearate | 1 |
| PEG-100 stearate | 1 |
| PEG-32 | 5 |
| KOH | 4.6 |
| Cocamidopropyl betaine | 1.5 |
| AP Sphere-1 | 5 |
| Total content | 100 |

[Preparation of Sample and Mimetic Skin Pores]
Sample: Standard fine particulate matter (SRM 1650b)
Solution concentration: 5% in deionized water or triglyceride (TG) oil
Area of mimetic skin pore frame: 2.5 cm×1.25 cm (size of one mimetic skin pore: circular shape having a diameter of 200 μm)
[Test Method]
1) 0.1 g of an fine particulate matter sample is applied uniformly to a mimetic skin pore frame.
2) The state of applied fine particulate matter is checked and photographed (10 shots) by using an optical microscope (magnification: ×4).
3) 1 g of a foam cleansing formulation and 0.5 mL of water are applied.
4) The formulation is rubbed by using fingers 30 times and is washed with flowing water.
5) Water is removed with Kimtech (wiper) or dried naturally.
6) The state of cleansing is checked (10 shots) by using an optical microscope (magnification: ×4).
[Analysis of Effect of Cleansing (Removing) Fine Particulate Matter]
The photographic images are analyzed by using an image analysis program (image-pro). Particularly, the image position is aligned before/after using the product, a common region is cropped and extracted, and then the value of area is analyzed based on the total area in each image. Herein, a decrease in the corresponding value (total area value of black pixels corresponding to fine particulate matter, pix^2) suggests that fine particulate matter in the skin pores is removed (cleaned).

Referring to FIG. 13A and FIG. 13B, it can be seen that even the fine particulate matter in the skin pores is removed completely, after carrying out washing treatment with the cleansing foam and observing the residual fine particulate matter. It can be seen from the image analysis that the area of the fine particulate matter sample in the mimetic skin pore is significantly reduced by 99.941% after applying and washing the cleansing foam formulation (13B), as compared to the state before cleansing (13A). This suggests that AP Sphere-1 can provide a practical effect of removing fine particulate matter even in the case of an actual formulation.

Test Example 8—Evaluation of Adsorption Capability Depending on Inorganic Particles ($TiO_2$)

As a control of AP Sphere-1 impregnated with $TiO_2$, particles free from $TiO_2$ were prepared by using 95 g of a biodegradable polymer and 5 g of a cationic polymer. This is intended to set the content of a cationic polymer having a critical function in realizing a fine dust-adsorbing effect through ionic bonding to the same content of 5 g.

Figure 14A:
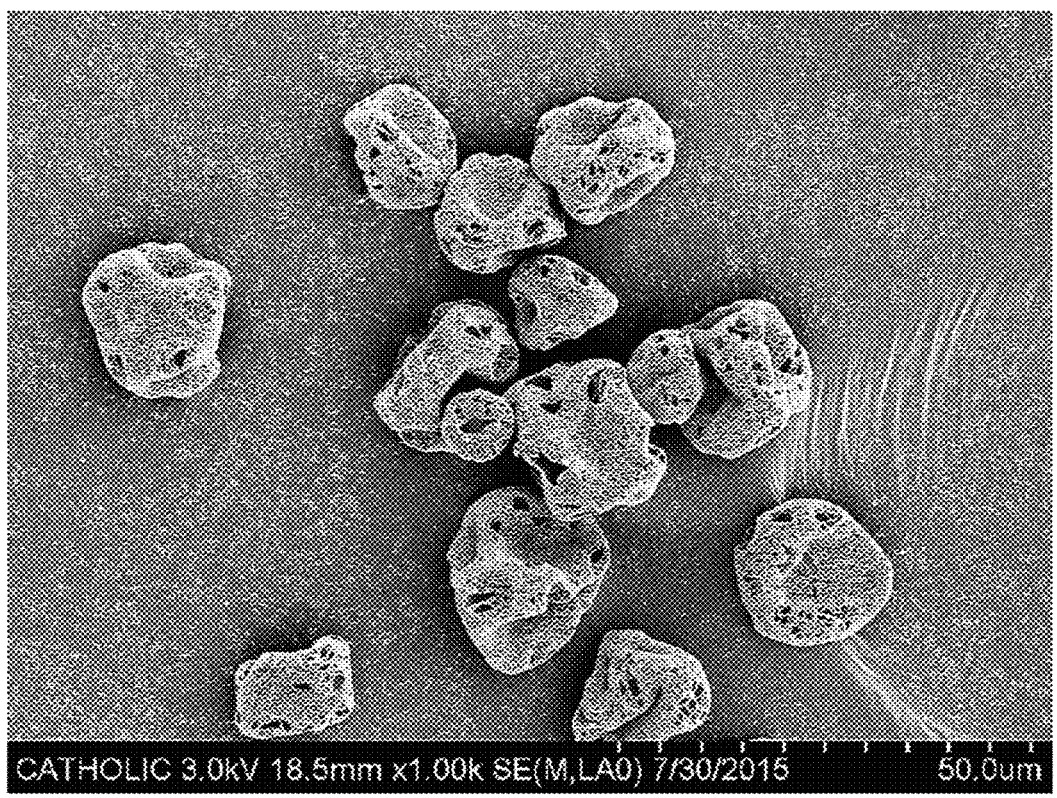
FIG. 14A and FIG. 14B are electron microscopic images of AP Sphere (free from $TiO_2$) according to an embodiment of the present disclosure.
Figure 14B:
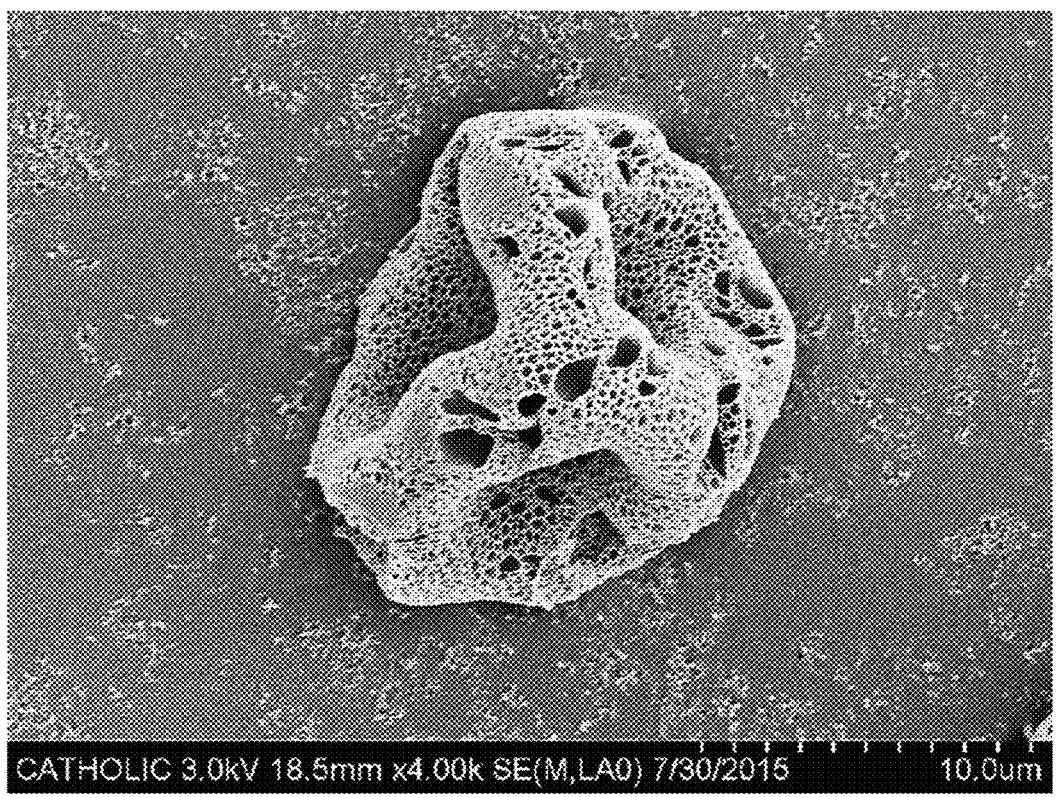

After observing the particles with an electronic microscope, it is shown that when using no inorganic powder functioning as a support, the polymer particles are shrunk during the spray drying to provide particles having a deformed shape (FIG. 14A and FIG. 14B). Such particles show a significantly low oil absorption of merely 0.13 mL/g and provide significantly low fine particulate matter adsorption capability. Therefore, it can be seen that impregnation with inorganic particles functioning as a support is essentially required to retain the particles without deformation and to ensure porosity according to an embodiment of the present disclosure.

Example 2—Preparation of Porous Composite Powder for Adsorption of Fine Dust (AP Sphere-2)

Figure 15:
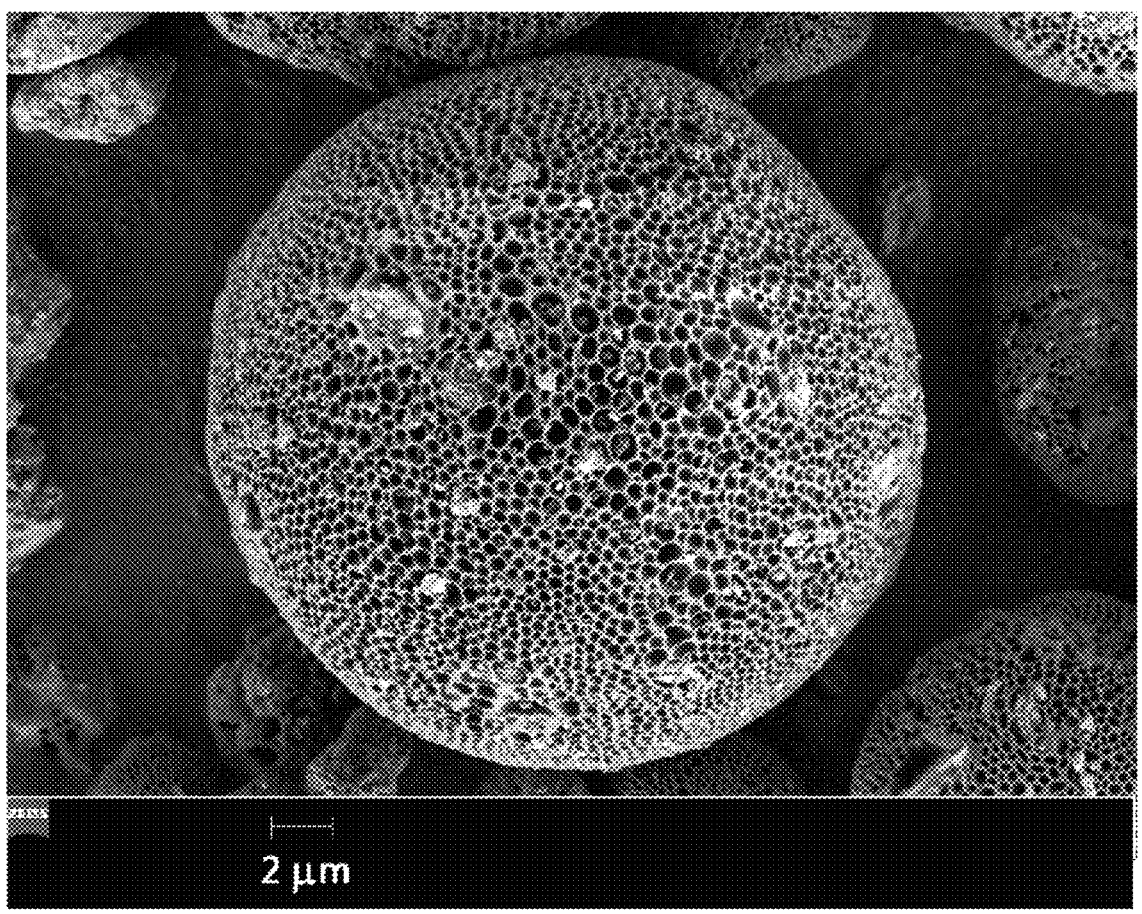
FIG. 15 is an electron microscopic image of the porous composite powder according to an embodiment of the present disclosure.

Porous composite powder (AP Sphere-2) for adsorption of fine dust was prepared by using volcanic ash and silica instead of $TiO_2$ as inorganic particles. Composite powder (Volcanic Plus, AP Sphere-2) as shown in FIG. 15 was obtained by adding 1 wt % of a cationic polymer (PQ10) to 45 wt % of volcanic ash, 30 wt % of silica (Lucidsil) and 24 wt % of a biodegradable polymer (PLGA) through the same spray drying process as AP Sphere-1. After analyzing the composite powder with an electronic microscope, it can be seen that the composite powder is impregnated homogeneously with volcanic ash and silica particles, while maintaining a porous structure (FIG. 15).

Figure 19:
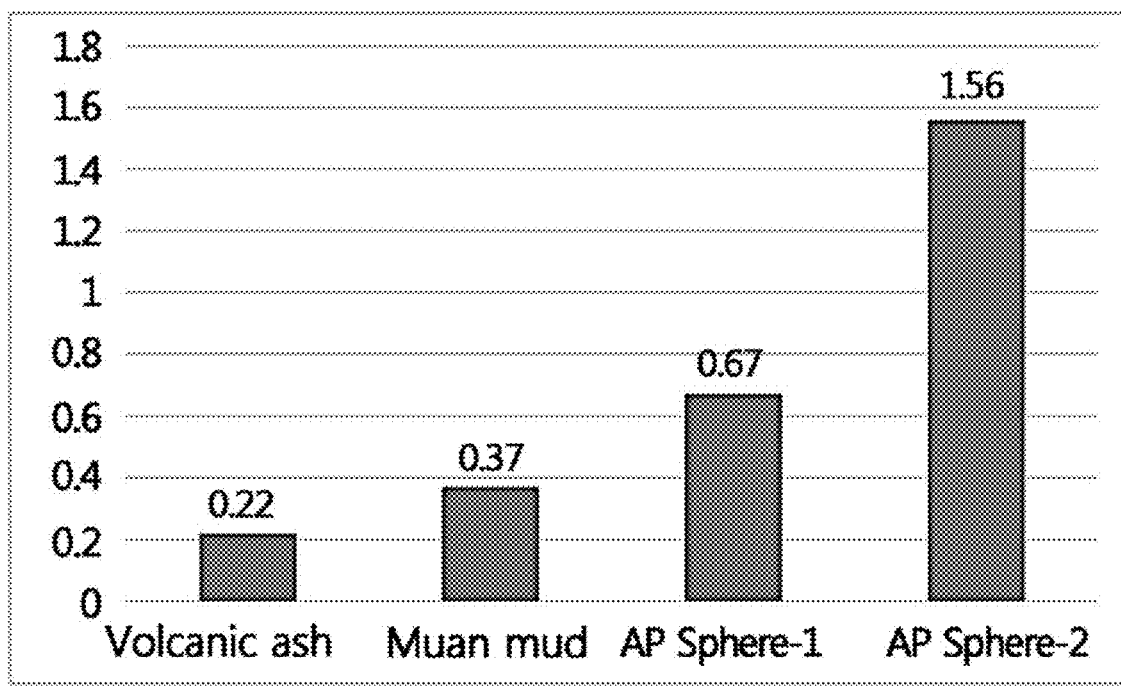
FIG. 19 shows the result of determination of oil absorption (mL/g) of the porous composite powder according to an embodiment of the present disclosure.

In addition, the oil absorption was analyzed in the same manner as Test example 2. As shown in FIG. 19, it can be seen that AP Sphere-2 shows a significantly increased oil absorption of 1.56 mL/g under the effect of silica (Lucidsil) having high oil adsorption, in addition to a porous structure.

Test Example 9—Determination of Zeta Potential of Porous Composite Powder

Figure 16:
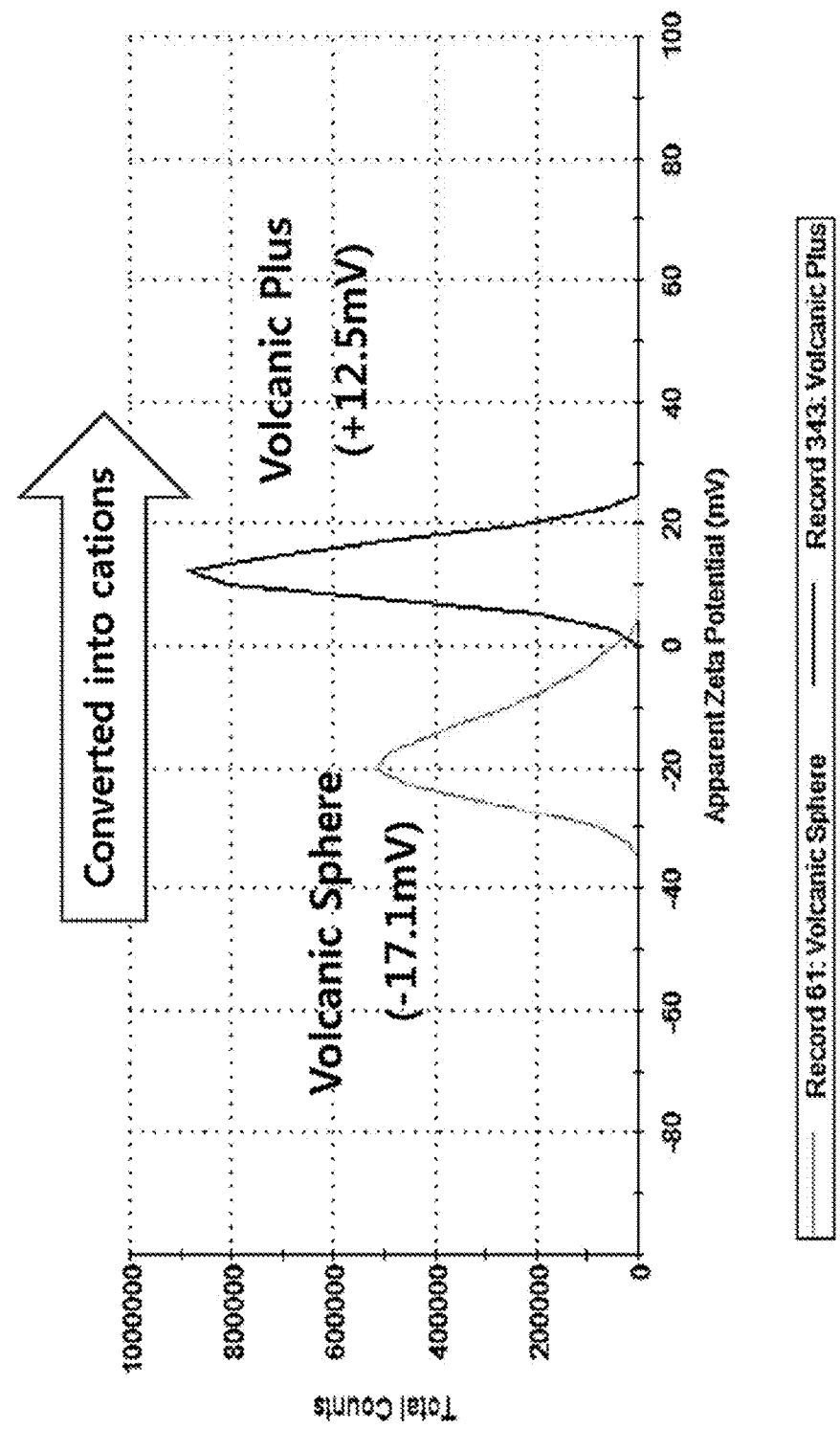
FIG. 16 shows the result of determination of zeta potential of the porous composite powder according to an embodiment of the present disclosure.

After measuring zeta potential, Volcanic Plus (AP Sphere-2) containing PQ10 added thereto is positively charged and shows a surface charge of +12.5 mV, while Volcanic Sphere having the same composition but free from PQ10, shows a surface charge of −17.1 mV (FIG. 16).

Test Example 10—Evaluation of Adsorption Capability

Figure 17A:
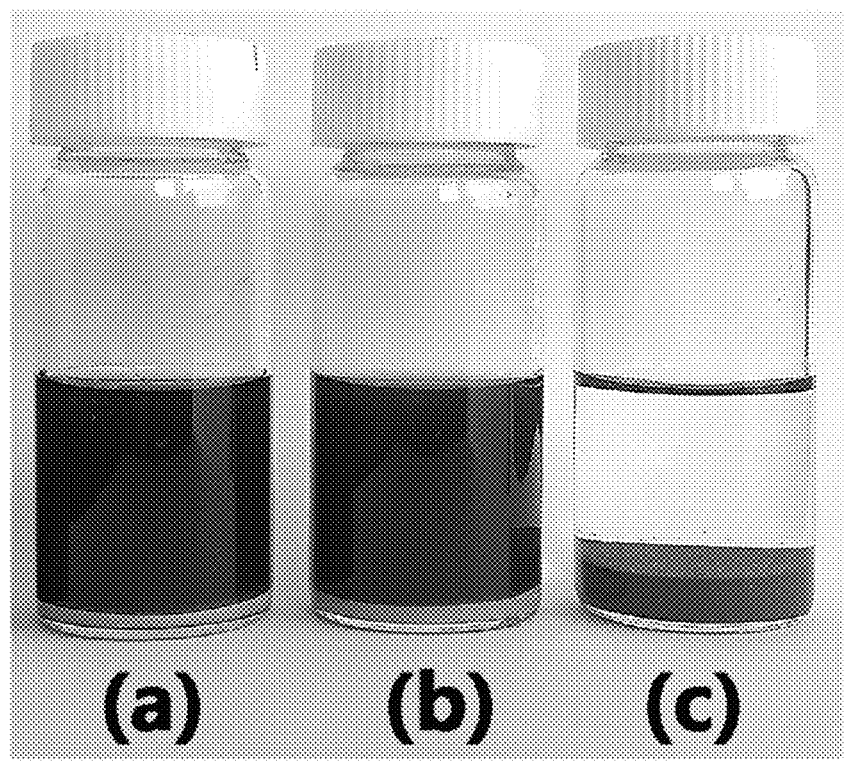
FIG. 17A to FIG. 17C show the results of determination of fine particulate matter adsorption performance of the porous composite powder according to an embodiment of the present disclosure.
Figure 17B:
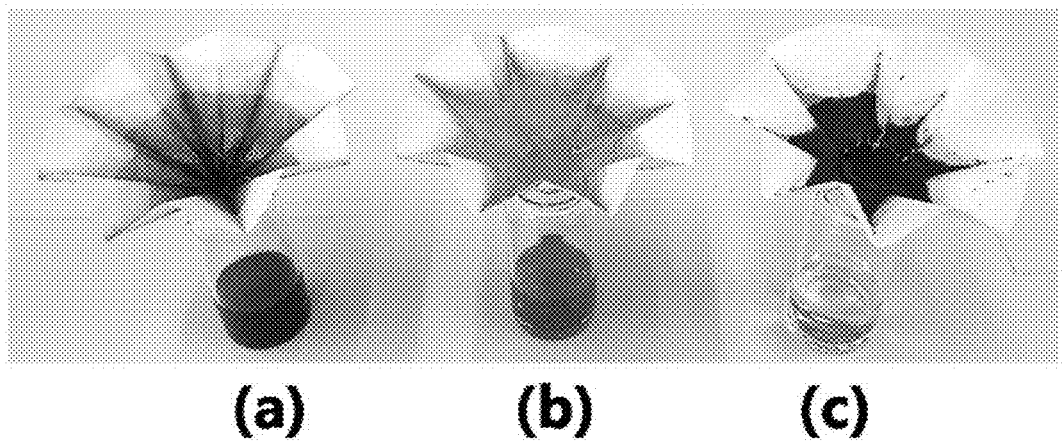
Figure 17C:
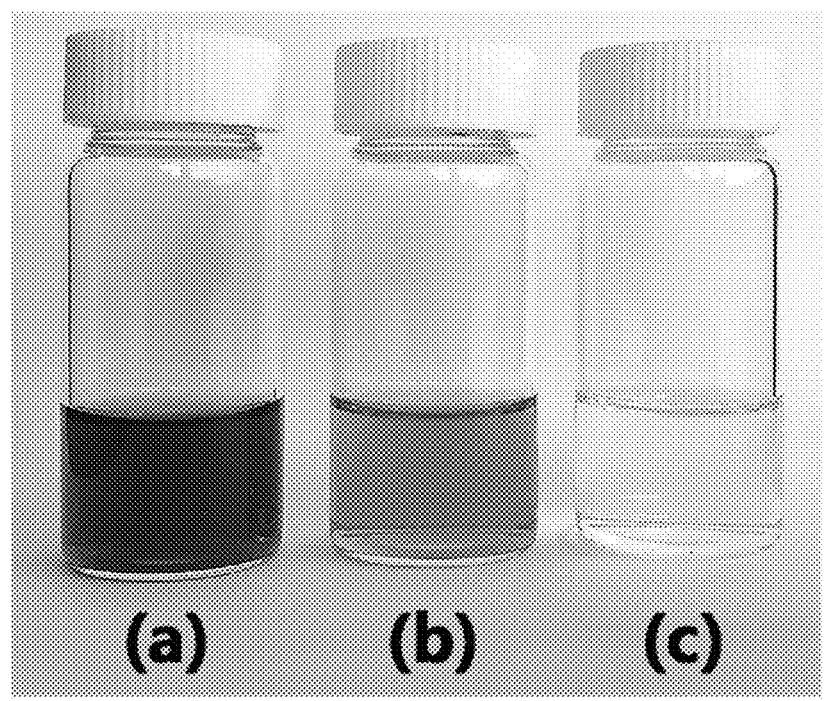

Volcanic Plus (AP Sphere-2) and Volcanic Sphere free from PQ10 were tested in terms of fine particulate matter adsorption in the same manner as Test Example 3. The test results are shown in FIG. 17A to FIG. 17C, which correspond to the result after introduction of powder, agitation and standing (17A), the result after filtering with filter paper (17B), and the result of filtrate (17C). In each drawing, the samples correspond to the non-treated sample (a), Volcanic Sphere (b) and Volcanic Plus (AP Sphere-2)(c).

The fine particulate matter adsorption test results have a similar tendency to the results of AP Sphere-1, and AP Sphere-2 shows an excellent effect. It can be seen that positively charged Volcanic Plus (AP Sphere-2) shows a higher effect of adsorbing and settling fine particulate matter as compared to negatively charged Volcanic Sphere (FIG. 17A to FIG. 17C).

Figure 18:
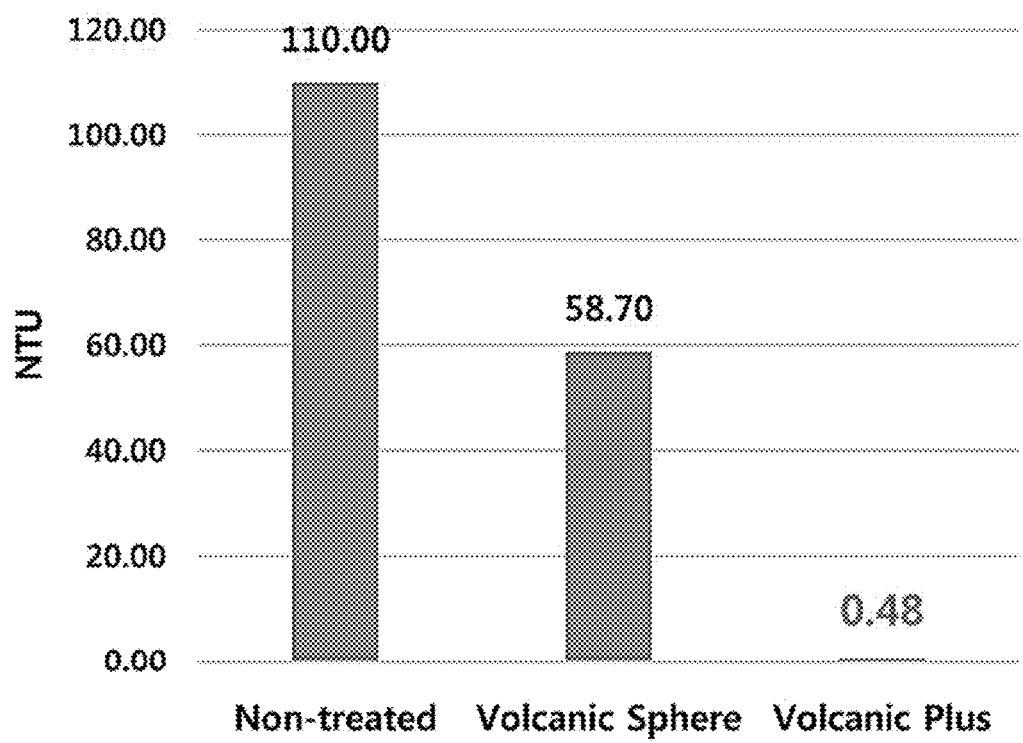
FIG. 18 shows the result of determination of transmittance of the porous composite powder according to an embodiment of the present disclosure.

After measuring the transmittance of each filtrate by using the turbidimeter as shown in FIG. 8A in order to carry out quantitative evaluation, it can be seen that the effect of adsorbing fine particulate matter of Volcanic Plus (AP Sphere-2) is at least 122 times higher than the effect of Volcanic Sphere. In the case of the filtrate of Volcanic Plus (AP Sphere-2), it shows a transmittance of 0.48 NTU, which is lower than the transmittance standard of domestic edible drinking water of 0.5 NTU (FIG. 18).

EMBODIMENTS

Embodiment 1: Porous composite powder for adsorption of fine dust, including:
a biodegradable polymer;
a cationic polymer; and
inorganic particles.

Embodiment 2: The porous composite powder for adsorption of fine dust as defined in Embodiment 1, wherein the biodegradable polymer and the cationic polymer form a composite on the surface of the porous composite powder, inside of the porous composite powder, or both.

Embodiment 3: The porous composite powder for adsorption of fine dust as defined in Embodiment 1 or 2, which is positively charged.

Embodiment 4: The porous composite powder for adsorption of fine dust as defined in any one of Embodiments 1 to 3, which has a zeta potential of 1 mV or more.

Embodiment 5: The porous composite powder for adsorption of fine dust to as defined in any one of Embodiments 1 to 4, which has a size of 50 µm or less.

Embodiment 6: The porous composite powder for adsorption of fine dust as defined in any one of Embodiments 1 to 5, which has a pore size of 10 nm to 1 µm.

Embodiment 7: The porous composite powder for adsorption of fine dust as defined in any one of Embodiments 1 to 6, which has a porosity of 30-80%.

Embodiment 8: The porous composite powder for adsorption of fine dust as defined in any one of Embodiments 1 to 7, wherein the biodegradable polymer is at least one selected from the group consisting of polylactic acid (PLA), polyglycolic acid (PGA), polylactic-co-glycolic acid (PLGA), polycaprolactone (PCL), cellulose and derivatives thereof.

Embodiment 9: The porous composite powder for adsorption of fine dust as defined in any one of Embodiments 1 to 8, wherein the cationic polymer is at least one selected from the group consisting of polyquaternium-based compounds, cationic guar gum derivatives, chitosan and polylysine.

Embodiment 10: The porous composite powder for adsorption of fine dust as defined in any one of Embodiments 1 to 9, wherein the cationic polymer is at least one selected from the group consisting of Polyquaternium-4, Polyquaternium-6, Polyquaternium-7, Polyquaternium-10, Polyquaternium-11, Polyquaternium-22, Polyquaternium-24, Polyquaternium-37, Polyquaternium-39 and Polyquaternium-100.

Embodiment 11: The porous composite powder for adsorption of fine dust as defined in any one of Embodiments 1 to 10, wherein the inorganic particle is at least one selected from the group consisting of $TiO_2$, ZnO, iron oxide, mica, sericite, volcanic ash, silica and mud.

Embodiment 12: The porous composite powder for adsorption of fine dust as defined in any one of Embodiments 1 to 11, wherein the inorganic particle is $TiO_2$.

Embodiment 13: The porous composite powder for adsorption of fine dust as defined in any one of Embodiments 1 to 12, which includes 3-60 wt % of a biodegradable polymer, 0.1-10 wt % of a cationic polymer and 35-90 wt % of inorganic particles, based on the total weight of the porous composite powder.

Embodiment 14: The porous composite powder for adsorption of fine dust as defined in any one of Embodiments 1 to 13, which adsorbs fine dust having a particle diameter of 2.5 µm or less.

Embodiment 15: A method for adsorbing fine dust, including applying a composition including the porous composite powder as defined in any one of Embodiments 1 to 14 onto the skin.

Embodiment 16: The method for adsorbing fine dust as defined in Embodiment 15, wherein the composition includes the porous composite powder in an amount of 1-30 wt % based on the total weight of the composition.

Embodiment 17: The method for adsorbing fine dust as defined in Embodiment 15 or 16, wherein the composition is a cosmetic composition.

Embodiment 18: The method for adsorbing fine dust as defined in Embodiment 17, wherein the cosmetic composition is at least one selected from the group consisting of cleansing cream, cleansing foam and cleansing water.

Embodiment 19: A method for preparing the porous composite powder for adsorption of fine dust as defined in any one of Embodiments 1 to 14, to including the steps of:
preparing a solution including a biodegradable polymer and a cationic polymer;
dispersing inorganic particles into the solution including a biodegradable polymer and a cationic polymer; and
spray drying the solution including the inorganic particles dispersed therein.

Embodiment 20: The method for preparing the porous composite powder for adsorption of fine dust as defined in Embodiment 19, wherein the spray drying is carried out at room temperature.

Embodiment 21: The method for preparing the porous composite powder for adsorption of fine dust as defined in Embodiment 19 or 20, wherein the solution including the inorganic particles dispersed therein is agitated during the spray drying.

Embodiment 22: The method for preparing the porous composite powder for adsorption of fine dust as defined in any one of Embodiments 19 to 21, wherein the solvent of the solution including the biodegradable polymer and the cationic polymer is at least one selected from the group consisting of anhydrous dichloromethane, ethanol and acetone.

Embodiment 23: The method for preparing the porous composite powder for adsorption of fine dust as defined in any one of Embodiments 19 to 22, which further includes a washing and drying step, after the spray drying step.

DESCRIPTION OF DRAWING NUMERALS

10 Heater
20 Nozzle

30 Drying Chamber
40 Cyclone
50 Product vessels
60 Aspirator
70 Filter

The invention claimed is:

1. Porous composite powder for adsorption of fine dust, comprising:
   a biodegradable polymer;
   a cationic polymer; and
   inorganic particles,
   wherein the biodegradable polymer and the cationic polymer form a composite on the surface and inside of the porous composite powder, wherein the inorganic particles are homogeneously dispersed on the surface and/or inside of the porous composite powder,
   wherein the inorganic particle is at least one selected from the group consisting of $TiO_2$, ZnO, mica, sericite, and, silica,
   wherein the porous composite powder comprises the cationic polymer in an amount of 0.1-10 wt. % based on the total weight of the porous composite powder and wherein:
   i. the porous composite powder is positively charged;
   ii. the porous composite powder has a zeta potential of 1 mV or more;
   iii. the porous composite powder has a size of 50 μm or less;
   iv. the porous composite powder has a pore size of 10 nm to 1 μm;
   v. the porous composite powder has a porosity of 30-80%; and
   wherein the biodegradable polymer is at least one selected from the group consisting of polylactic acid (PLA), polyglycolic acid (PGA), polylactic-co-glycolic acid (PLGA), polycaprolactone (PCL), cellulose and derivatives thereof, and
   wherein the cationic polymer is at least one selected from the group consisting of cationic guar gum derivatives, chitosan and polylysine.

2. The porous composite powder for adsorption of fine dust according to claim 1, which comprises 3-60 wt % of the biodegradable polymer, and 35-90 wt % of the inorganic particles, based on the total weight of the porous composite powder.

3. The porous composite powder for adsorption of fine dust according to claim 1, which adsorbs fine dust having a particle diameter of 2.5 μm or less.

4. A method for adsorbing fine dust, comprising applying a composition including the porous composite powder as defined in claim 1 onto the skin.

5. The method for adsorbing fine dust according to claim 4, wherein the composition comprises the porous composite powder in an amount of 1-30 wt % based on the total weight of the composition.

6. The method for adsorbing fine dust according to claim 4, wherein the composition is a cosmetic composition.

7. The method for adsorbing fine dust according to claim 6, wherein the cosmetic composition is at least one selected from the group consisting of cleansing cream, cleansing foam and cleansing water.

* * * * *